(12) United States Patent
Pybus et al.

(10) Patent No.: US 9,047,787 B2
(45) Date of Patent: Jun. 2, 2015

(54) PERFUSION METHOD AND APPARATUS

(75) Inventors: Andrew Pybus, Haymarket (AU); John Begg, Forestville (AU); Richard Morris, Lilyfield (AU); James Craig Herbert, Earlwood (AU); Vladimir Ilic, Concord West (AU); Stephen Ronald Fuller, Valley Heights (AU)

(73) Assignee: TERUMO CARDIOVASCULAR SYSTEMS CORP., Ann Arbor, MI (US)

( * ) Notice: Subject to any disclaimer, the term of this patent is extended or adjusted under 35 U.S.C. 154(b) by 1386 days.

(21) Appl. No.: 12/095,371

(22) PCT Filed: Nov. 21, 2006

(86) PCT No.: PCT/AU2006/001754
§ 371 (c)(1),
(2), (4) Date: Jan. 15, 2009

(87) PCT Pub. No.: WO2007/062453
PCT Pub. Date: Jun. 7, 2007

(65) Prior Publication Data
US 2009/0305214 A1 Dec. 10, 2009

(30) Foreign Application Priority Data

Nov. 30, 2005 (AU) .................................. 2005906716

(51) Int. Cl.
*G09B 23/28* (2006.01)
*A61M 5/44* (2006.01)
(Continued)

(52) U.S. Cl.
CPC ............... *G09B 23/285* (2013.01); *A61M 5/44* (2013.01); *A61M 5/486* (2013.01); *A61M 5/445* (2013.01);
(Continued)

(58) Field of Classification Search
CPC ......... A61M 5/44; A61M 5/445; A61M 5/46; A61M 5/48; A61M 5/321; A61M 4/481; A61M 5/484; A61M 5/486; A61M 5/488; A61F 2007/12; A61F 7/126; G09B 23/28; G09B 23/285; G09B 23/30
USPC ........................... 434/262, 267, 268; 604/113
See application file for complete search history.

(56) References Cited

U.S. PATENT DOCUMENTS 4,678,460 A * 7/1987 Rosner ........................ 604/113
5,679,005 A * 10/1997 Einstein ......................... 800/8
(Continued)

FOREIGN PATENT DOCUMENTS

DE 40435452 A1 6/1992
DE 4141129 A1 6/1993
(Continued)

OTHER PUBLICATIONS

STIC non-patent search of Jul. 22, 2014.*
(Continued)

*Primary Examiner* — Nikolai A Gishnock
(74) *Attorney, Agent, or Firm* — Gael Diane Tisack, Esq.; Darryl Newell; MacMillan, Sobanski & Todd

(57) ABSTRACT

Apparatus use with a perfusion system, the apparatus including a subject simulator for simulating subject. The subject simulator includes a circulatory system having an inlet line for receiving fluid from the perfusion system, an outlet line for transferring fluid to the perfusion system, at least on sensor for sensing at least one fluid property and at least one control device coupled to at least one of the inlet line and the outlet line. In use this, allows the control device to manipulate the at least on fluid property based at least partially on signals from the at least one sensor, to thereby simulate a least one of compliance and resistance of the simulated subject.

1 Claim, 15 Drawing Sheets

(51) Int. Cl.
*A61M 5/48* (2006.01)
*A61M 5/32* (2006.01)
*A61M 5/46* (2006.01)
*G09B 23/30* (2006.01)

(52) U.S. Cl.
CPC ............... *A61M 5/484* (2013.01); *A61M 5/48* (2013.01); *A61M 5/321* (2013.01); *G09B 23/28* (2013.01); *A61M 5/46* (2013.01); *A61M 5/488* (2013.01); *G09B 23/30* (2013.01); *G09B 23/303* (2013.01)

(56) References Cited

U.S. PATENT DOCUMENTS

| | | | |
|---|---|---|---|
| 5,846,224 A * | 12/1998 | Sword et al. | 604/113 |
| 6,234,804 B1 * | 5/2001 | Yong | 434/267 |
| 6,273,728 B1 * | 8/2001 | van Meurs et al. | 434/268 |
| 6,463,930 B2 | 10/2002 | Biondi et al. | |
| 6,503,087 B1 | 1/2003 | Eggert et al. | |
| 6,783,328 B2 * | 8/2004 | Lucke et al. | 417/43 |
| 6,921,267 B2 | 7/2005 | Van Oostrom et al. | |
| 7,364,563 B2 * | 4/2008 | Lucke et al. | 604/6.15 |
| 7,611,478 B2 * | 11/2009 | Lucke et al. | 604/6.15 |
| 7,646,901 B2 * | 1/2010 | Murphy et al. | 382/128 |
| 2001/0019818 A1 * | 9/2001 | Yong | 434/262 |
| 2002/0150476 A1 * | 10/2002 | Lucke et al. | 417/2 |
| 2004/0101814 A1 | 5/2004 | Morris et al. | |
| 2005/0100873 A1 * | 5/2005 | Meythaler et al. | 434/267 |
| 2005/0119600 A1 * | 6/2005 | Lucke et al. | 604/6.15 |
| 2008/0195022 A1 * | 8/2008 | Lucke et al. | 604/4.01 |

FOREIGN PATENT DOCUMENTS

| | | |
|---|---|---|
| WO | WO0226286 A2 | 4/2002 |
| WO | WO 2004070994 A2 * | 8/2004 |

OTHER PUBLICATIONS

"Sydney Perfusion Simulator", www.manbit.com, Dec. 12, 1998, downloaded from the internet www.web.archive.org/web/*http://www.manbit.com/ on Jan. 3, 2007.

"On the Utilization of Automatic Control Systems Within a Perfusion System" Lucke et al., Mar. 2003; available at http://www.minnetronix.com/newspub/publications/perfusionsystems.html.

* cited by examiner

PERFUSION METHOD AND APPARATUS

BACKGROUND OF THE INVENTION

The present invention relates to a method and apparatus for use with a perfusion system and in particular for training or assessing a perfusionist, testing perfusion equipment and demonstrating a perfusion process using a heart/lung machine.

DESCRIPTION OF THE PRIOR ART

The reference to any prior art in this specification is not, and should not be taken as, an acknowledgment or any form of suggestion that the prior art forms part of the common general knowledge.

It is estimated that coronary heart disease will become the single biggest public health problem in the world by 2020. As a result of this the number of surgical procedures performed on the heart is increasing, and consequently there is a need for an increasing number of medical personnel trained in performing appropriate procedures.

One particular process, known as cardiopulmonary bypass or perfusion is the process of replacing the actions of the heart and lungs with a mechanical device during cardiac surgery.

The process involves placing a line in the right atrium of the patient to allow deoxygenated blood pumped from the heart to the lungs to be diverted through a HLM, also known as a heart and lung machine (HLM), which operates to oxygenate the blood before pumping the blood back into the body via a line connected to the aorta.

In addition to this, the perfusionist is also responsible for using the HLM to provide cardioplegia to thereby cause the heart to stop, allowing surgery to be performed. The cardioplegia solution may need to be chilled and it is necessary for the perfusionist to control this.

It is also necessary for the perfusionist to be able to monitor the patient, understand the patient's response to the perfusion process, and control the HLM accordingly.

Management of cardiopulmonary bypass is therefore a complex time critical task and the risks of failing to maintain effective perfusion include patient injury or death.

An explanation for this lies in the potential for sudden major failures of the perfusion system demanding a prompt response from the perfusionist who due to lack of appropriate training may lack the technical capability or work experience to cope with unexpected medical emergency. Both of these factors can be linked to the inadequate or infrequent current teaching methods.

In particular, current training techniques are basic and generally involve having the perfusionist watch a limited number of procedures, before performing procedures and then ultimately training other individuals during procedures. Whilst a high degree of theoretical qualification is required, it is evident that very little actual practice of emergency responses is ever undertaken.

As a result of this, when previously unencountered situations arise it is necessary for the perfusionist to use purely theoretical knowledge in overcoming the situation. This is particularly a problem when faults occur such as obstructions occurring in the lines to the patient, power failures, equipment failure, or the like.

A further issue is that when new equipment is designed, there are only limited systems available to test the operation of the equipment before it must be used in a procedure to adequately assess its ability to provide adequate perfusion under all circumstances. This in turn leads to a risk associated with the introduction of new equipment into perfusion procedures.

SUMMARY OF THE PRESENT INVENTION

In a first broad form the present invention provides apparatus use with a perfusion system, the apparatus including a subject simulator for simulating a subject, the subject simulator including a circulatory system having:
 a) an inlet line for receiving fluid from the perfusion system;
 b) an outlet line for transferring fluid to the perfusion system;
 c) at least one sensor for sensing at least one fluid property; and,
 d) at least one control device coupled to at least one of the inlet line and the outlet line, wherein in use, the control device manipulates the at least one fluid property based at least partially on signals from the at least one sensor, to thereby simulate at least one of compliance and resistance of the simulated subject.

Typically the apparatus includes a control system for controlling the at least one control device to thereby manipulate the at least one fluid property in accordance with signals from the at least one sensor.

Typically the at least one fluid property includes at least one of:
 a) fluid flow rate;
 b) fluid pressure; and,
 c) fluid temperature.

Typically the at least one sensor includes at least one of:
 a) a temperature sensor;
 b) a flow transducer;
 c) a pressure sensor; and,
 d) a fluid level sensor.

Typically the subject simulator simulates subject compliance using at least one of:
 a) a reservoir for receiving fluid from the inlet line and providing fluid to the outlet line; and,
 b) a compliance chamber positioned in the inlet line.

Typically the at least one control device includes at least one of:
 a) an inlet valve positioned in the inlet line for simulating an arterial line kink;
 b) a resistive valve positioned in the outlet line for generating a varying resistance to, at least one of:
  i) prevent air entering the perfusion system;
  ii) simulate a venous line blockage; and,
  iii) simulate oscillation of fluid flow in the outlet line;
 c) an air entrainment valve positioned in the outlet line for simulating venous line air entrainment;
 d) a temperature controller for controlling the temperature of fluid in the outlet line;
 e) a blood loss controller for simulating blood loss;
 f) an arterial resistance control device for generating a resistance to flow in the inlet line, thereby at least partially simulating the resistance of the circulatory system of the simulated subject; and,
 g) one or more fault devices for simulating equipment failures.

Typically the temperature controller includes a reservoir for holding a volume of fluid for moderating the temperature of fluid in the outlet line.

Typically the arterial resistance control device includes at least one of:
 a) a resistor positioned in the inlet line; and,
 b) a heart pump for urging fluid in a reverse direction along the inlet line.

Typically the arterial resistance control device generates a pressure waveform representing cardiac waveforms in the inlet line.

Typically the blood loss controller includes:
  a) a blood loss reservoir connected to the inlet line; and,
  b) at least one of:
    i) a blood loss pump for pumping fluid from the inlet line to the blood loss reservoir; and,
    ii) a valve for allowing fluid to drain from the inlet line into the blood loss reservoir.

Typically the perfusion system includes an oxygenator, and wherein the fault device includes at least one of:
  a) a gas flow valve for simulating gas flow failure;
  b) an oxygenator leak valve for simulating a leak from the oxygenator; and,
  c) oxygenator air injection for simulating injection of air into the oxygenator.

Typically the fault device includes a relay for simulating power failures in at least one of:
  a) the perfusion system;
  b) a subject monitor; and,
  c) a subject heater/cooler.

Typically the subject simulator includes a cardioplegia circuit including:
  a) a cardioplegia reservoir;
  b) a cardioplegia inlet for cardioplegia solution from the perfusion system and transferring the fluid to the reservoir;
  c) a cardioplegia outlet line for transferring cardioplegia solution from the cardioplegia reservoir to the perfusion system;
  d) at least one cardioplegia control device for manipulating the flow of cardioplegia solution through the simulator; and,
  e) at least one cardioplegia sensor for sensing properties of the cardioplegia solution.

Typically the at least one cardioplegia control device includes at least one of:
  a) an antegrade resistance;
  b) at least one retrograde resistance; and,
  c) a valve for allowing simulation of either antegrade or retrograde cardioplegia.

Typically the control system is for:
  a) receiving signals from the at least one sensor;
  b) determining at least one parameter relating to a simulated subject health status using at least one predetermined model; and,
  c) generating at least one control signal to selectively activate the at least one control device.

Typically the processing system generates the at least one control signal in accordance with at least one of:
  a) at least one failure mode;
  b) at least one scenario; and,
  c) at least one input command from an operator.

Typically the control system includes:
  a) a processing system for generating a control string; and,
  b) a controller for generating the at least one control signal using the control string.

Typically the control system includes a processing system for:
  a) receiving signals from the at least one sensor;
  b) determining at least one parameter relating to a subject health status using the received signal; and,
  c) using the determined parameter, at least one of:
    i) displaying the at least one parameter; and,
    ii) controlling at least one control device.

Typically the processing system is for:
  a) receiving input commands from an operator; and,
  b) controlling at least one control device using the input commands.

Typically the processing system is for:
  a) displaying control representations; and,
  b) determining input commands based on an operator's manipulation of the control representations.

Typically the processing system includes a store for storing scenario data, and wherein the processing system is for:
  a) determining, using the scenario data, at least one scenario; and,
  b) controlling, using the scenario, at least one of:
    i) the at least one control device;
    ii) at least one cardioplegia control device; and,
    iii) at least one fault device.

Typically the apparatus further includes a display coupled to the control system and wherein the control system is for:
  a) determining a procedure stage; and,
  b) displaying representations of the procedure stage on the display.

Typically the control system is for determining the procedure stage using signals from the at least one sensor and scenario data.

Typically the apparatus further includes an end station coupled to the control system, the end station being for allowing an individual to control one or more aspects of the perfusion process.

Typically the perfusion system is a HLM (Heart Lung Machine).

Typically the apparatus is used for at least one of:
  a) training medical personnel;
  b) demonstrating medical procedures;
  c) testing medical equipment; and,
  d) assessing medical personnel.

In a second broad form the present invention provides a method of simulating a subject in a perfusion system, the method including providing a subject simulator including a circulatory system having:
  a) an inlet line for receiving fluid from the perfusion system;
  b) an outlet line for transferring fluid to the perfusion system;
  c) at least one sensor for sensing at least one fluid property; and,
  d) at least one control device coupled to at least one of the inlet line and the outlet line, wherein the method includes, in the control device, manipulating the at least one fluid property based at least partially on signals from the at least one sensor, to thereby simulate at least one of compliance and resistance of the simulated subject.

Typically the method is performed using the apparatus of the first broad form of the invention.

In a third broad form the present invention provides a computer program product for use in simulating a subject in a perfusion system, the computer program product being used as part of a subject simulator including a circulatory system having:
  a) an inlet line for receiving fluid from the perfusion system;
  b) an outlet line for transferring fluid to the perfusion system;
  c) at least one sensor for sensing at least one fluid property; and,
  d) at least one control device coupled to at least one of the inlet line and the outlet line, wherein the computer program product causes the control device to manipulate the at least one fluid property based at least partially on signals from the at least one sensor, to thereby simulate at least one of compliance and resistance of the simulated subject.

In a fourth broad form the present invention provides apparatus for use with a perfusion system, the apparatus including a control system coupled to a subject simulator for:
  a) receiving signals from at least one sensor provided in a circulatory system of the subject simulator, the at least one sensor sensing at least one fluid property;
  b) determining at least one parameter relating to a simulated subject health status using at least one predetermined model; and,
  c) generating control signals to selectively activate at least one control device in the circulatory system to thereby manipulate at least one fluid property, to thereby simulate at least one of compliance and resistance of the simulated subject.

Typically the at least one predetermined model includes at least one of:
  a) a physiological model;
  b) a pharmacokinetic model; and,
  c) a pharmacodynamic model.

Typically the control system generates control signals in accordance with at least one of:
  a) at least one failure mode;
  b) at least one scenario; and,
  c) at least one input command from an operator.

Typically the control system includes:
  a) a processing system for generating a control string; and,
  b) a controller for generating the at least one control signal using the control string.

Typically the control system includes a processing system for:
  a) receiving signals from the at least one sensor;
  b) determining at least one parameter relating to a subject health status using the received signal; and,
  c) using the determined parameter, at least one of:
    i) displaying the at least one parameter; and,
    ii) controlling at least one control device.

Typically the processing system is for:
  a) receiving input commands from an operator; and,
  b) controlling at least one control device using the input commands.

Typically the processing system is for:
  a) displaying control representations; and,
  b) determining input commands based on an operator's manipulation of the control representations.

Typically the processing system includes a store for storing scenario data, and wherein the processing system is for:
  a) determining, using the scenario data, at least one scenario; and,
  b) controlling, using the scenario, at least one of:
    i) the at least one control device;
    ii) at least one cardioplegia control device; and,
    iii) at least one fault device.

Typically the apparatus further includes a display coupled to the control system and wherein the control system is for:
  a) determining a procedure stage; and,
  b) displaying representations of the procedure stage on the display.

Typically the control system is for determining the procedure stage using signals from the at least one sensor and scenario data.

Typically the apparatus further includes an end station coupled to the control system, the end station being for allowing an individual to control one or more aspects of the perfusion process.

Typically the apparatus is used with apparatus according to the first broad form of the invention.

In a fifth broad form the present invention provides a method for use with a perfusion system, the method including, in a control system coupled to a subject simulator:
  a) receiving signals from at least one sensor provided in a circulatory system of the subject simulator, the at least one sensor sensing at least one fluid property;
  b) determining at least one parameter relating to a simulated subject health status using at least one predetermined model; and,
  c) generating control signals to selectively activate at least one control device in the circulatory system to thereby manipulate at least one fluid property, to thereby simulate at least one of compliance and resistance of the simulated subject.

Typically the method is performed using the apparatus of the third broad form of the invention.

In a sixth broad form the present invention provides a computer program product for use with a perfusion system, the computer program product including computer executable code which when executed on a suitable control system coupled to a subject simulator, causes the control system to:
  a) receive signals from at least one sensor provided in a circulatory system of the subject simulator, the at least one sensor sensing at least one fluid property;
  b) determine at least one parameter relating to a simulated subject health status using at least one predetermined model; and,
  c) generate control signals to selectively activate at least one control device in the circulatory system to thereby manipulate at least one fluid property, to thereby simulate at least one of compliance and resistance of the simulated subject.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
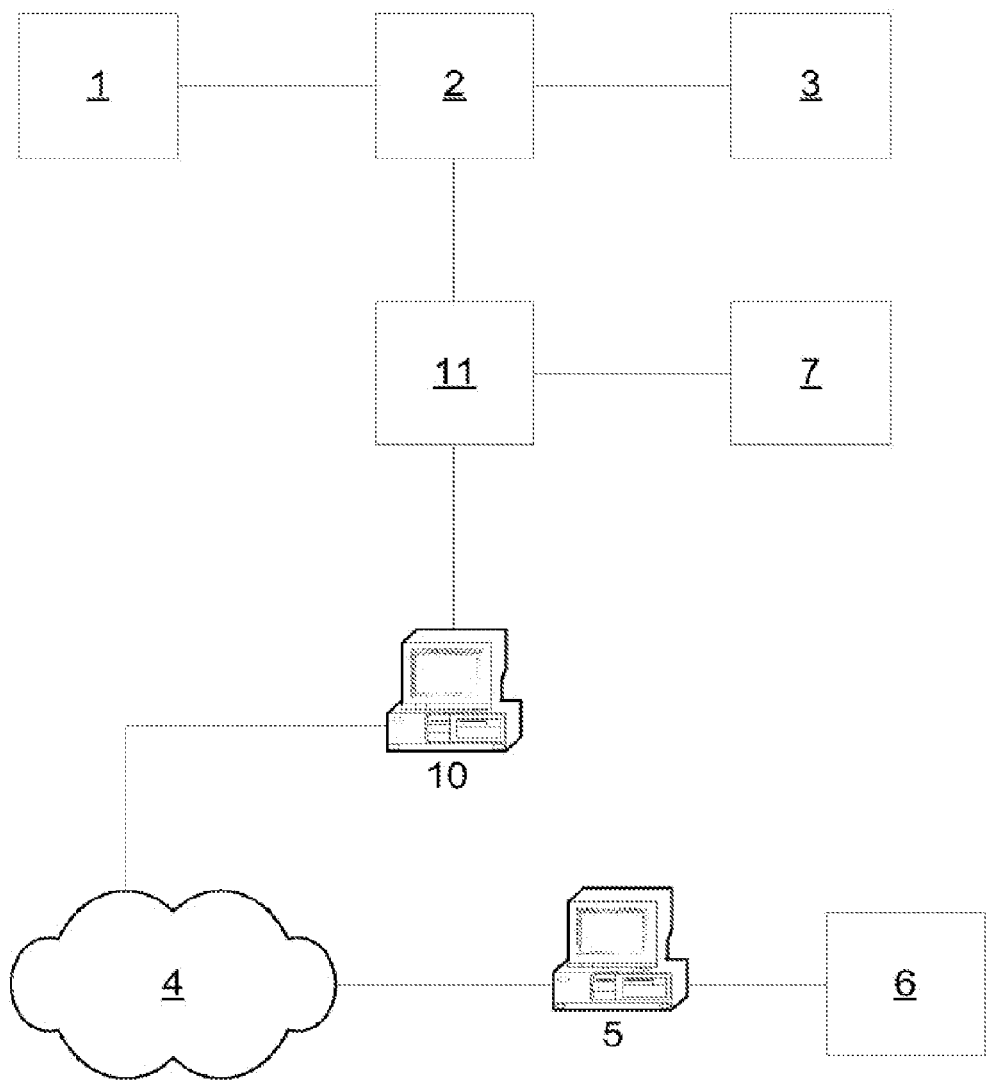
FIG. 1 is a schematic of an example of a system used in training a perfusionist.

An example of apparatus for training a perfusion will now be described with reference to FIG. 1. In particular, as shown the apparatus includes an HLM 1 connected to a patient simulator 2, which is in turn connected to a patient monitor 3.

A processing system 10 is coupled to a controller 11, which is in turn coupled to the patient simulator 2 and ancillary equipment shown generally at 7.

An optional end station 5 and display 6 may be provided for use by a trainee, in which case the end station 5 is coupled to the processing system 10 via a suitable communications link 4, such as a communications network, wired or wireless connection, or the like.

In use, the patient simulator 2 operates to simulate the behaviour of a patient undergoing heart surgery to thereby allow the perfusionist to operate the HLM 1 in accordance with normal techniques which would be required during heart surgery procedures. The patient simulator 2 utilises a hydraulic system to represent blood flow through a patient, and to allow a cardioplegia process to be performed.

The processing system 10, using the controller 11, operates to control the patient simulator 2 to thereby allow the patient simulator to simulate different stages of heart procedures, as well as to allowing for faults to be simulated, through the use of the ancillary equipment 7, and the patient simulator 2.

The patient monitor 3 and sensors in the patient simulator 2, operate to provide feedback regarding the current health status of the simulated patient.

This allows the HLM 1 and the patient monitor 3 to be formed from standard hospital equipment, thereby helping ensure that the perfusionist becomes familiar with the operation of a HLM as well as to familiarise themselves with perfusion techniques.

In use, a trainer uses the processing system 10 to control the patient simulator 2 and ancillary equipment by generating appropriate control strings that are interpreted by the controller 11. The controller 11 then generates control signals which are applied to the patient simulator and ancillary equipment as required.

Figure 2:
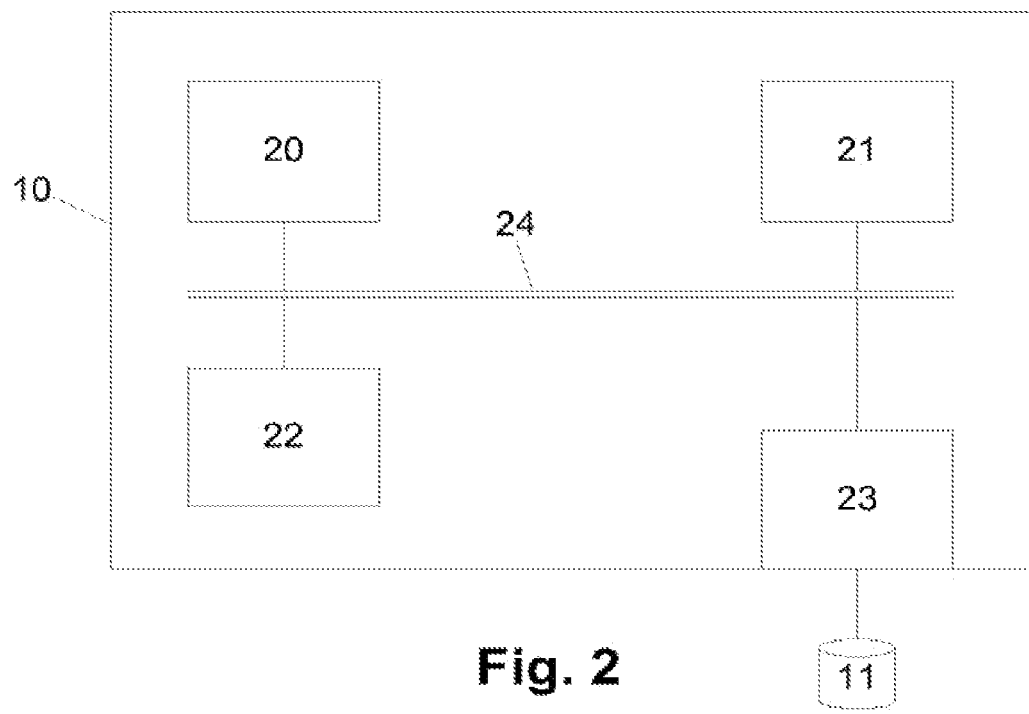
FIG. 2 is a schematic of an example of the processing system of FIG. 1.

An example of a suitable processing system 10 is shown in FIG. 2. As shown the processing system 10 includes a processor 20, a memory 21, an input/output device 22, such as a keyboard and display or the like, and an external interface 23, coupled together via a bus 24. In use the external interface 23 may be coupled to the controller 11, as well as providing connections to the communications network 4. It will therefore be appreciated that the external interface 23 may be formed from one or more communications devices or interfaces, and only a single interface is shown for clarity.

Accordingly, the processing system 10 may be any form of processing system, such as a computer server, a network server, a web server, a desktop computer, a lap-top or the like. Alternative specialised hardware may be used.

The computer end station 5 may be used to provide feedback to the trainee perfusionist with the optional display 6 being used to display images of real surgery to the perfusionist so they can understand the context behind a particular training scenario.

Figure 3:
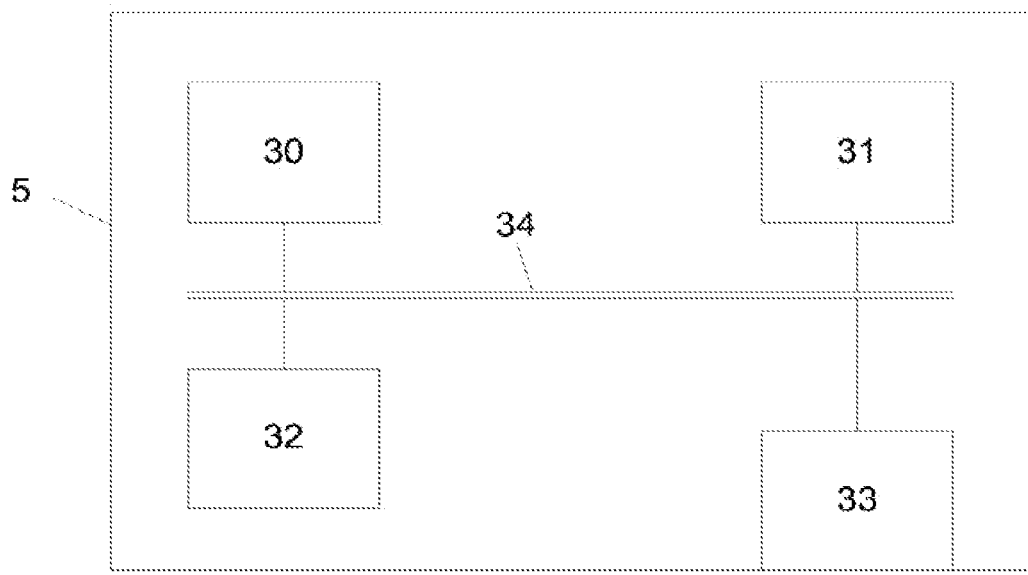
FIG. 3 is a schematic of an example of the end station of FIG. 1.

Accordingly, as shown in FIG. 3, the end station 5 may be formed from a processor 30, a memory 31, an input/output device 32 and an external interface 33, coupled together via a bus 34. Again the external interface 33 may be used to provide a connection to the communications network 4. Accordingly the end station 5 may be any form of computer system such as a desktop computer, lap-top, specialised hardware or the like.

In one example, the processing system 10 and the end station 5 communicate via a TCP/IP network. The components can be networked using 10/100/1000 Mbps Ethernet (IEEE 802.3) or a wireless 802.11a/b/g network. The software architecture will also support the system configurations where the processing system 10 and the end station 5 are connected via the Internet.

Figure 5:
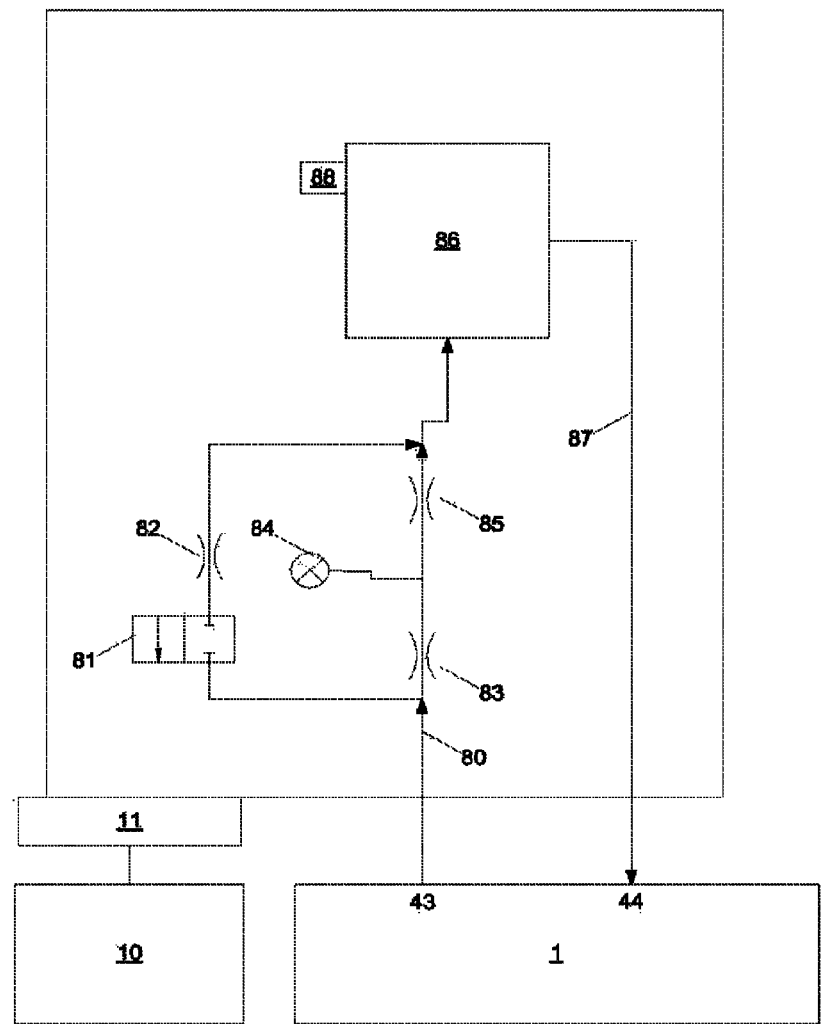
FIG. 5 is a schematic of an example of the cardioplegia circuit of the patient simulator of FIG. 1.
Figure 6:
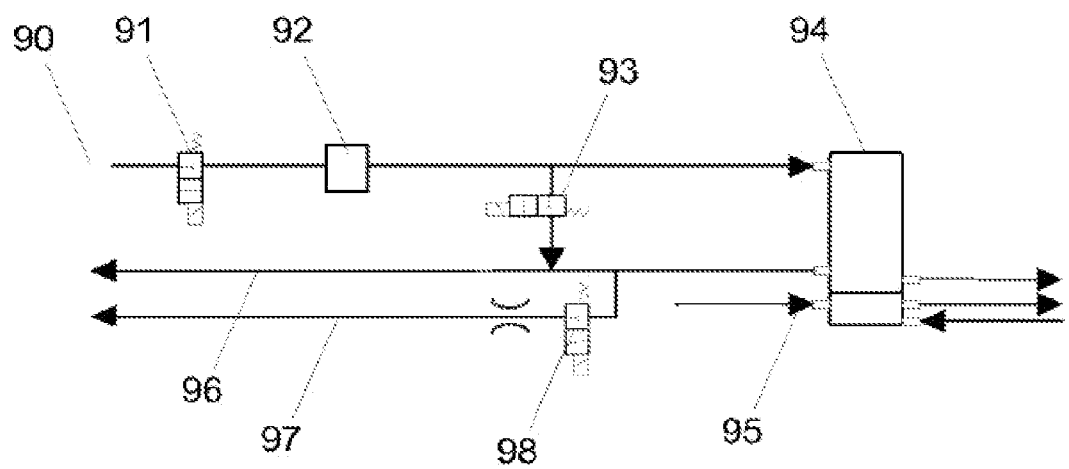
FIG. 6 is a schematic of an example of the oxygenator circuit of FIG. 1.

An example of the configuration of the patient simulator 2 will now be described in more detail with respect to FIGS. 4 to 6.

Figure 4:
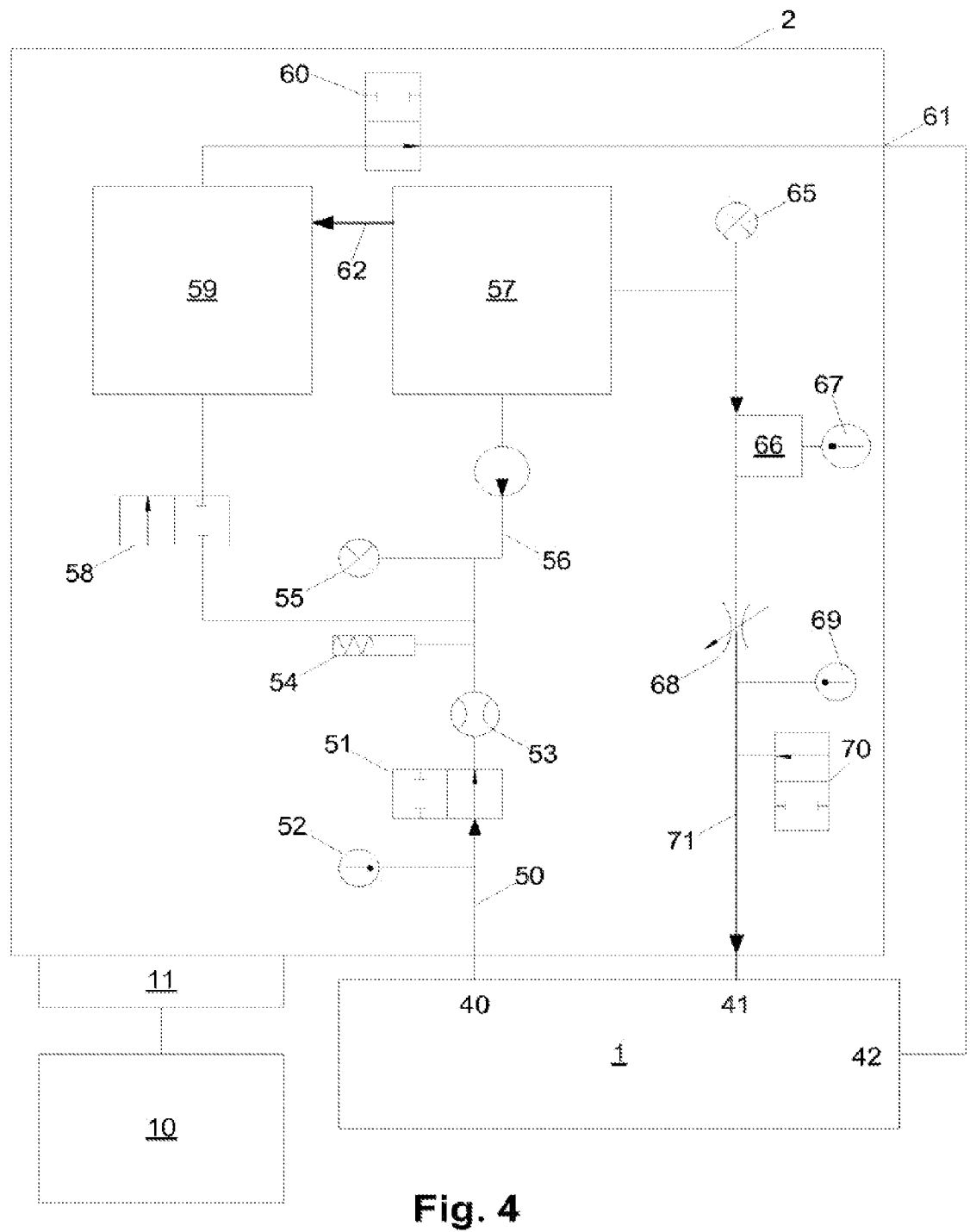
FIG. 4 is a schematic of an example of the cardiopulmonary circuit of the patient simulator of FIG. 1.

In particular, FIG. 4 is a schematic diagram of the connection of the HLM 1 to the circulatory system simulated in the patient simulator 2. In this regard, the HLM 1 includes an outlet 40 which would normally be coupled to the patient's aorta and an input 41 which would normally be coupled to the right atrium of the patients heart to receive deoxygenated blood.

As shown the patient simulator includes an input line 50 coupled to the HLM outlet 40. The input line 50 includes an arterial line kink valve 51, an arterial line temperature sensor 52, a flow meter 53, an arterial line compliance chamber 54, a heart pump 56 and an arterial line pressure sensor 55. The heart pump 56 is arranged in a reverse direction to provide a controlled resistance to flow from the HLM outlet 40 as shown.

The heart pump 56 is coupled to a venous capacitor fluid reservoir 57. A leak valve 58 is provided to allow fluid to be drained from the input line into a pleural cavity fluid reservoir 59. The pleural cavity reservoir 59 is connected to an outlet 61 to allow fluid to drain either into the HLM 1, via an inlet 42. This is controlled via a solenoid valve 60.

An overflow channel 62 is typically provided from the venous capacitor reservoir 57 into the pleural cavity reservoir 59.

The venous capacitor reservoir is coupled to the inlet 41 via a venous return line 71, which includes a central venous pressure sensor 65, a thermal reservoir 66 which is coupled to a temperature sensor 67, and a venous resistor 68. Positioned downstream of the venous resistor 68 is a temperature sensor 69 and an air entrainment valve 70 as shown.

An example of the cardioplegia circuit for the perfusion system will now be described with reference to FIG. 5.

As shown the perfusion system includes a cardioplegia outlet 43 and a cardioplegia inlet 44. The cardioplegia outlet 43 is coupled to a cardioplegia line 80, which includes an ante/retro solenoid valve 81 and an antegrade resistance 82, provided in parallel with first and second retrograde resistances 83, 85 and a coronary sinus pressure sensor 84. The cardioplegia line 80 is connected to a cardioplegia reservoir 86 which is in turn connected to the cardioplegia inlet 44 via a cardioplegia return line 87. A level sensor 88 monitors the level of fluid in the cardioplegia reservoir 86.

An example of the oxygenator circuit will now be described with reference to FIG. 6.

The oxygenator circuit includes an oxygen supply 90, a gas flow failure valve 91, an air/oxygen mixer alarm 92, and oxygenator air injector 93, coupled to an oxygenator 94. The oxygenator receives blood via an inlet 95, and is coupled to a blood outlet line 96. The blood outlet line is also coupled to a blood leak line 97 having an oxygenator leak valve 98, and the oxygenator air injector 93, as shown.

The processing system 10 operates to obtain signals from the temperature and pressure sensors 52, 67, 69, 55, 65, and the flow meter 53 to thereby monitor fluid conditions within the arterial line and the venous return line. This allows the processing system 10 to make an assessment of patient health status, as well as to control the patient simulator 2 to simulate different scenarios.

In use, the patient simulator 2 uses water within the hydraulic system to simulate blood. When the patient simulator 2 is initially connected to the HLM 1, the venous return line 71 is clamped with the heart pump 56 operating to generate a varying back pressure in the arterial fluid line 50, to thereby represent the blood pressure waveforms of the beating heart. The water level in the venous capacitor reservoir 57 represents the volume of blood within the patient.

Once the HLM 1 begins to pump water into the patient simulator input line 50, the clamp is released and pressure is generated in the input line 50, dependent on the level of resistance generated by the heart pump 56. Water pressure generated in the venous capacitor reservoir 57 urges water along the venous return line 71 into the HLM 1 via the inlet 41. The water is passed through an oxygenator within the HLM 1, as will be described in more detail below. The water is then provided, via the outlet 40 to the arterial line 50.

The processing system 10 controls the heart pump 56 and introduces appropriate resistance to mimic the body's resistance to blood flow, as well as to separately generate pressure waveforms representing the beating heart.

As cardioplegia is applied to the patient simulator 2, via the cardioplegia line 80, the amplitude of the arterial pressure waveform, generated by the heart pump 56, changes in relation to the cardioplegia concentration in the heart.

Throughout this process, the simulated patient responsiveness can be manipulated by altering the operation of the line kink valve 51, the venous resistor 68, the thermal reservoir 66 and the air entrainment valve 70. These can be used to simulate various fault conditions during the heart process including a kink in the arterial line connecting the HLM outlet 40 to the aorta, variations in subject body temperature, variations in heart rate output and the presence of an air leak in the venous return line 71.

Additionally, activation of the leak valve 58 can be used to reduce the volume of fluid included in the arterial line, the venous return line and the venous capacitor fluid reservoir thereby mimicking blood loss within a patient.

The processing system 10 is able to operate the ante/retro valve 81 which, when open, allows all three resistances 82,83 and 85 to be connected to the HLM cardioplegia outlet 43. When ante/retro valve 81 is closed the retrograde resistances 83 and 85 only, are connected to the HLM cardioplegia outlet 43. The coronary sinus pressure sensor 84 then monitors the coronary sinus pressure for dangerous levels and for calculating cardioplegia flow rates. As cardioplegia flows through the cardioplegia line 80, pressure at the coronary sinus pressure sensor 84 and the cardioplegia reservoir 86 fluid level are monitored for inappropriate use of aortic root suction of fluid into the HLM 1.

The use of ancillary equipment 7, including relays, allows power supply failures to be mimicked, whilst use of the gas flow failure valve 91, oxygenator air injector 93, and oxygenator leak valve 98, allows issues with the oxygenator to be simulated.

Figure 7:
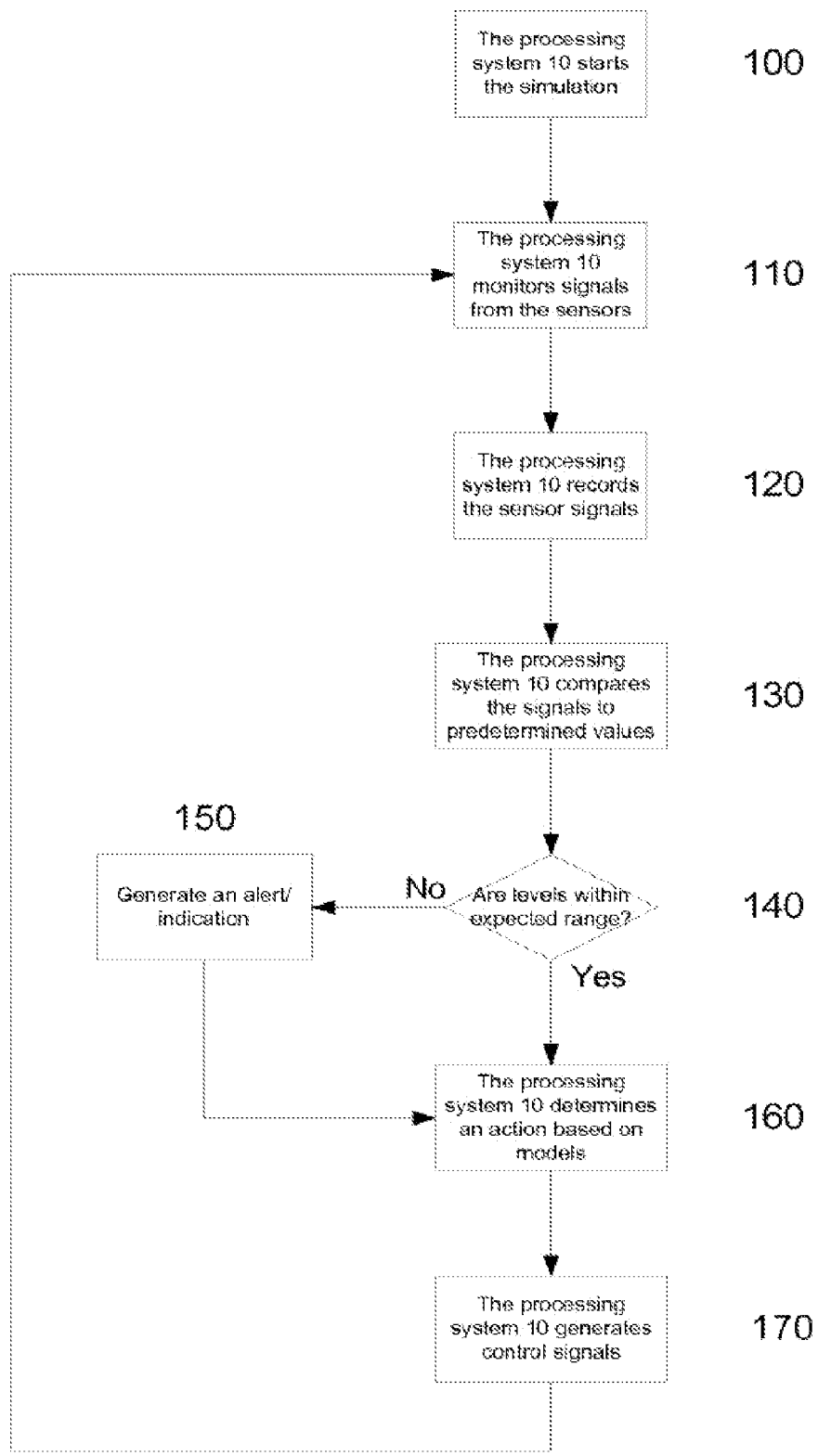
FIG. 7 is a flowchart of an example of a process for determining cardiac function.
Figure 8A:
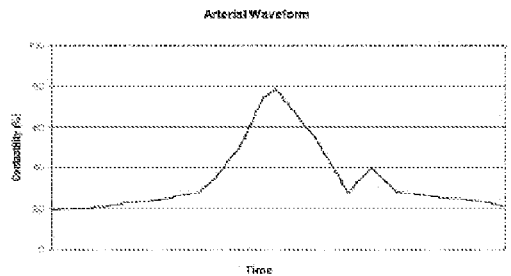
FIGS. 8A to 8L are examples of cardiac waveforms simulated by the patient simulator of FIG. 4.
Figure 8B:
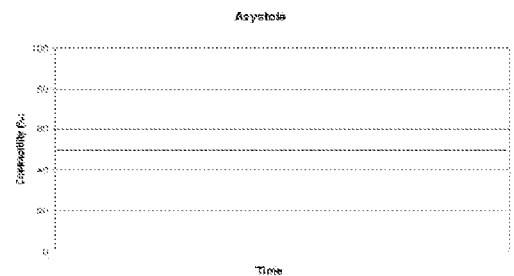
Figure 8C:
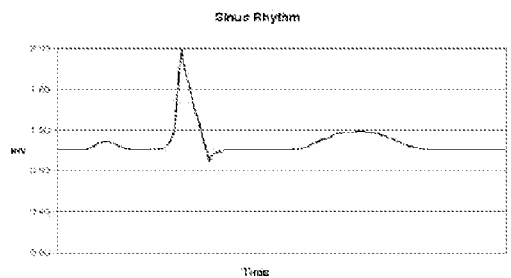
Figure 8D:
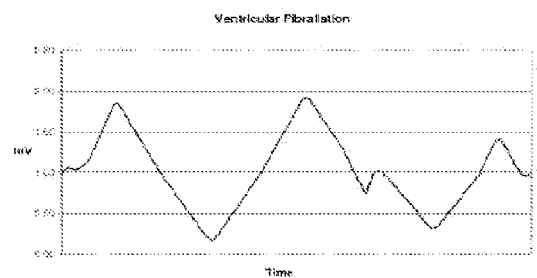
Figure 8E:
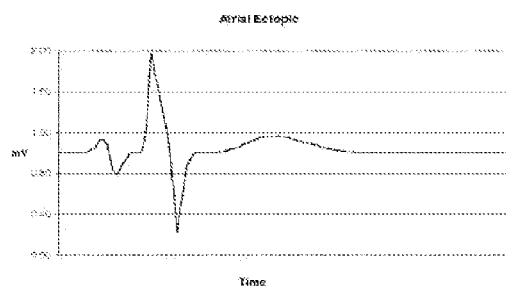
Figure 8F:
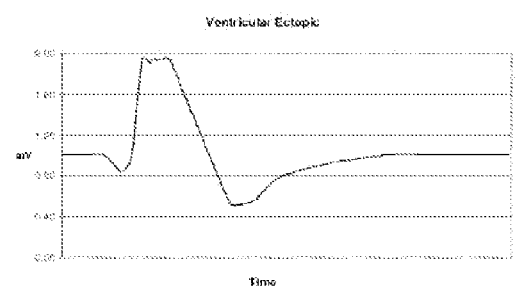
Figure 8G:
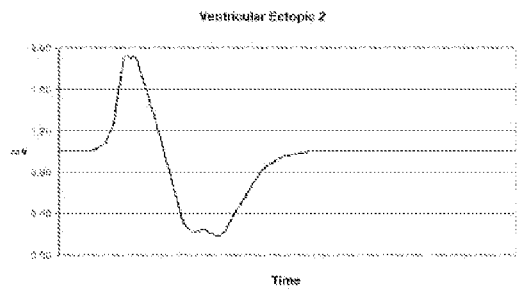
Figure 8H:
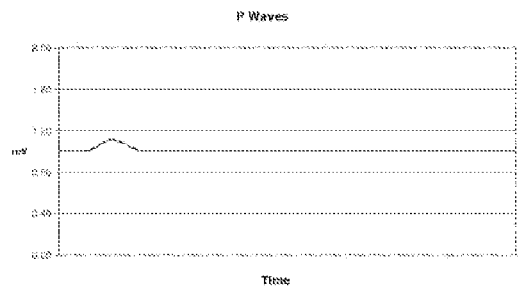
Figure 8I:
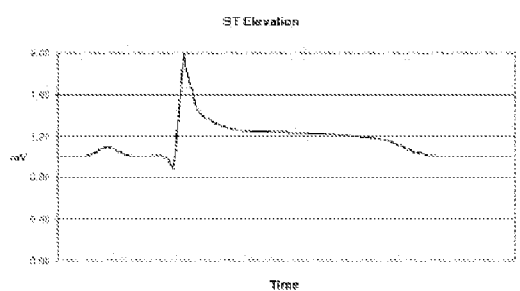
Figure 8J:
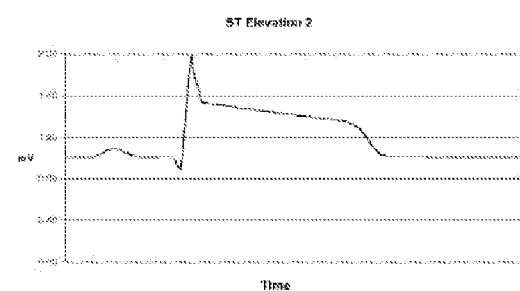
Figure 8K:
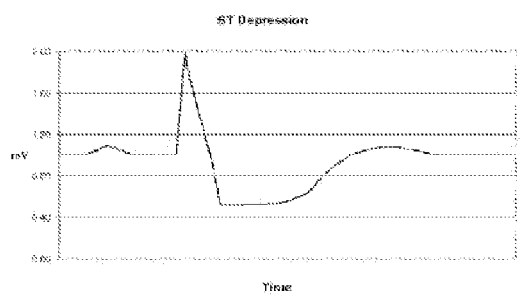
Figure 8L:
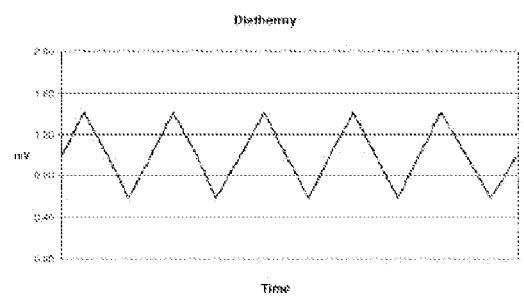

An example of the operation of the processing system 10 will now be described with reference to FIG. 7.

In particular, at step 100 the processing system 10 starts the simulation, which may be based on a scenario. Such scenarios may include an entire medical procedure such as an entire heart bypass operation, or may include a predetermined portion of a procedure, such as an oxygenator failure. The scenarios may be defined manually by a trainer using the processing system 10, may be stored in the form of predetermined profiles in the memory 21, or may use a combination of manual and automated steps.

At step 110 the processing system 10 monitors signals from the sensors typically operating to record these for subsequent analysis at step 120.

At step 130 the processing system 10 compares sensor readings to predetermined values stored in the memory 21 and determines whether these are in expected parameter ranges at 140.

If not, the processing system 10 can operate to generate an alert or an indication indicative of the fact that a problem is occurring with the procedure. Following this, or otherwise, the processing system 10 typically determines a response action based on the current health status of the simulated patient and different models.

Thus, the response action may be in the form of simply maintaining the patient in their current status to allow the perfusionist to perform the required perfusion actions. Alternatively the response action may include creating a fault or even presenting information to the perfusionist. This can include, for example, triggering the display of video content of a corresponding stage of the procedure, to allow the perfusionist to familiarise themselves with how different perfusion stages correspond to different stages in a surgical procedure.

At step 170 the processing system 10 typically operates to generate control signals to allow the patient simulator 2 to be controlled in an appropriate manner in accordance with the scenario.

This process is then repeated either until the scenario is completed or describes the simulated death of a patient.

Operation of each of the components will be described in more detail below.

Patient Simulator Operation

The patient simulator operates to generate a realistic circulatory system that can be perfused using a HLM and monitored using existing patient monitoring equipment.

To achieve this the simulator can incorporate appropriate hydraulic, electrical, physiological, pharmacokinetic and pharmacodynamic models and function as a complete 'patient substitute'. This is achieved based on the software control provided by the processing system 10, which allows the simulator to be used in the training of perfusionists and other medical or paramedical staff in the use of 'heart-lung' machines and related equipment.

An example of the elements used by the patient simulator to achieve this will now be described in more detail.

Venous Capacitor Reservoir

The venous capacitor reservoir represents:

the capacitive properties of the major veins and the RA (Right Atrium); and, the volume of the patient's blood that is available for siphoning into the HLM.

The properties required to achieve this are represented by:

$$V_{(t)} = \int \Sigma(q) dt \quad (1)$$

$$P_{cv} = \frac{1}{C} \int \Sigma(q) dt \quad (2)$$

where:

$\Sigma(q)$=sum of the flows into the major veins and RA
V=Volume of blood in the Venous Capacitor.
$P_{cv}$=Central Venous Pressure.
C=Capacitance due to compliance of veins and RA.

In general, the maximum volume is limited to:

$V_{max}$=1.5 L

If this volume is exceeded, the excess will flow into the pleural cavity via the overflow line 62. If an open container is used for the venous capacitor then a means of preventing the complete draining of the container is typically employed to prevent air entering the venous lines.

In use, the capacitive effect is simulated using the gravitational effect of the column of water in the reservoir. Accordingly, the properties can be defined by:

$$p_{cv} = \rho p h = \rho g \frac{V_{(t)}}{A} \quad (3)$$

$$C = \frac{A}{\rho g} \quad (4)$$

where: ρ=water density
g=acceleration due to gravity
h=height of water column
A=Plan area of Venous Capacitor
$P_{cv}$=0 mmHg at V=0 L.
$P_{cv}$=11 mmHg (15 cm $H_2O$, 1.47 kPa) at V=1.5 L.
This is equivalent to:
C=0.14 L/mmHg (0.10 cm $H_2O$/L, 1.05 *$10^{-6}$ $m^3$/Pa)

Central venous pressure is measured and transmitted to the controller for software calculation of nominal pump drive power.

Central venous pressure is also measured by an ELM transducer.

Heart Pump 56

The heart pump, located in the hydraulic system, is adapted to provide two functions, namely:
producing a pulsatile pressure waveform; and,
providing a constant pumping action to pump against the flow from the HLM to thereby simulate arterial resistance representing the resistance the HLM would see in the arterial line and patient.

The operation of the heart pump 56 is controlled by the processing system 10, which sends a command string to controller 11, which in turn generates control signals to control the operation of the pump.

The heart pump 56 draws fluid from the venous capacitor reservoir 57 and passes it through the aortic valve. It has the capacity to deliver up to 5 l/min. This peak capacity is reached against a load resistance of 18 mmHg·min/l.

The heart pump is typically capable of producing an outlet pressure of 200 mmHg (26 kPa) at zero flow. Its response time, is sufficiently fast to produce the required aortic pressure waveforms described below, and is typically self-priming to prevent air locks.

In one example, the control signals drive a 12V, 6 Amp load, with short-circuit output protection.

Pulsatile Flow

The pump's pulsatile output is a function of the depth of fluid in the venous capacitor reservoir, which represents the Central Venous Pressure (CVP), so that the output is zero when the fluid just covers the intake of the pump CVP=0 mmHg, and a maximum when the CVP>10 mmHg.

In use, the system is configured to operate with the intake being covered with fluid at all times. If air enters the pump, an air lock occurs and the output of the pump is severely degraded.

To generate the pulsatile flow, the processing system generates a command string containing the waveform to use, including the arterial pulse rate and the amplitude of the waveform. The controller 11 uses this string to access a look-up table, which in turn indicates the control signal that should be used to drive the heart pump 56. The control signal is updated throughout each beat to generate the required arterial waveforms.

ECG Signals

However, in addition to generating pulsatile flow as described above, the system also operates to generate electronic signals simulating ECG waveforms that would be generated by the patient. The electrical signals can be detected by the patient monitor 3, which then displays a corresponding ECG trace to the perfusionist in the normal way.

Typically the system is capable of simulating a number of different specific conditions, including:
Sinus Rhythm
Ventricular Fibrillation
Asystole
Atrial Ectopic
Ventricular Ectopic
Ventricular Ectopic2
P-wave only
ST Elevation
ST Elevation2
ST Depression
Diathermy This is achieved by generating ECG signals using waveforms similar to those set out in FIGS. 8A to 8L. These are generated separately to, but in synchronisation with the heart pump waveform. The ECG output will provide a connection point on the hydraulic system for any monitoring system using either a 3-lead or 5-lead ECG lead. This output should allow the monitoring equipment to detect a realistic ECG waveform.

Arterial Resistance

The arterial resistance represents the restriction imposed on the blood flow, principally by the arterioles, but including the entire circulatory system. It may vary depending on the patient and on the affect of medication administered during the operation.

The total resistance of the arterial and venous system is within the range of 5 to 25 mmHg·min/L (39 to 195 MPa·s/m3). A nominal value of 15 mmHg·min/L (117 MPa·s/m3) is suggested for a subject performing no muscular exercise.

The arterial resistance can be simulated by varying the mean heart pump speed under control of the processing system 10, after allowing for the resistance of the heart pump 56, the flow meter 53, the arterial line kink valve 51 and the pipes 50, 71. To achieve this the processing system sends a serial control string containing a resistance value to the controller 11, which then adds this value as a DC offset to the arterial waveform.

At zero pump speed, the maximum resistance to flow through the pump will be such that the minimum arterial resistance is not exceeded.

Arterial Compliance 54

The compliance of the major arteries has a capacitive affect on the pressure pulses emanating from the HLM peristaltic pump and the heart.

When the peristaltic pump is operating and the aorta is clamped off, the arterial pressure waveform is approximately sinusoidal. At an average pressure of 40 mmHg (5.3 kPa), the amplitude is approximately 2.5 mmHg (325 Pa).

When the heart pump is operating, the effect of the arterial compliance on the arterial pressure waveform can be modified by appropriate control of the heart pump. In cardio pulmonary bypass mode, the waveform will be affected by the system compliance and will comply with the above model properties.

Venous Resistor 68

With a nominal venous flow rate, the pressure surrounding the venous cannula is positive even though the pressure downstream of the cannula is negative. This is due to the pressure drop across the venous cannula. During coronary bypass procedures, if the blood pressure in the vena cava and right atrium drops, the walls of these organs may collapse onto the venous cannula, thereby inducing an oscillation (chatter) in the blood flow.

The venous line resistance 68, is typically formed from a stepper motor driven cam that occludes a ½" silicon tubing, located in the venous return line 71. This device will be used to regulate the CVP, generate venous line chatter and create a venous line kink. A position sensor will be used to determine when the valve is completely open or closed.

Figure 9:
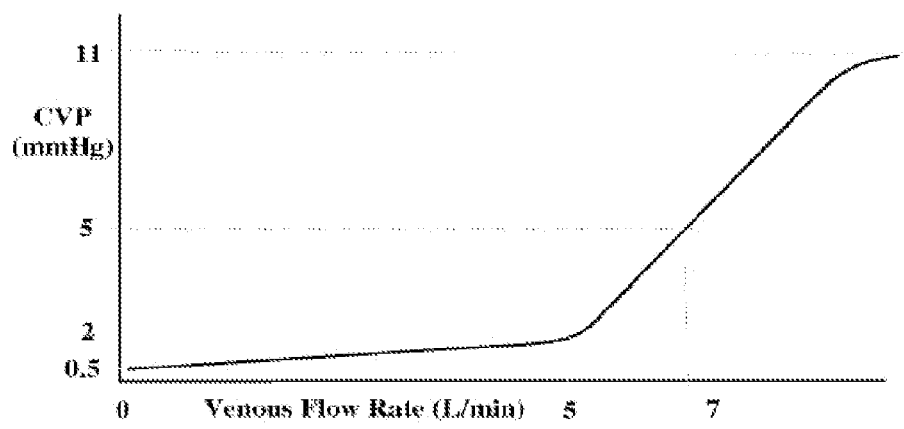
FIG. 9 is an example of a graph of the venous flow rate against cardio vascular pressure for the patient simulator of FIG. 4.

During normal operation the resistance of the venous resistor 68 is varied with flow to maintain the CVP as a function of steady flow rate as shown in FIG. 9, within 0.8 mmHg (1 cm H2O, 98 Pa). However, under control of the processing system 10, chatter can also be induced as required.

To achieve this the processing system 10 generates a serial control string containing the CVP value required to the controller 11, together with an indication of whether chatter is on or off, or whether a venous line kink is required. The controller 11 can use a proportional-integral-derivative (PID) controlled feedback loop to regulate the CVP and generate chatter or occlude the line completely in the case of a kink.

The controller is typically capable of driving the stepper motor in a stepping mode and completely occlude the tubing without the motor slipping.

Cardioplegia

During the surgery process, cardioplegia solution is introduced into the patient to alter the heart's ECG rhythms. This is typically performed to slow or stop the heart completely to allow the surgery to be performed. In practice, cardioplegia solution is injected into the root of the aorta between a cross clamp and the aortic valve (antegrade) or the coronary veins via the coronary sinus (retrograde). This enables it to perfuse the myocardium.

The aortic root suction can remove cardioplegia from the root of the aorta and, if the aortic cross clamp is released, blood can flush cardioplegia from the myocardium.

During aortic root suction approximately 300 ml of cardioplegia will be removed, after which air is entrained. The cardioplegia conditions are typically set by the following conditions:

Antegrade cardioplegia flow rate into the coronary arteries is nominally qca=200 ml/min when cardioplegia pressure at the HLM is 200 mmHg (27 kPa).

Retrograde cardioplegia flow rate into the coronary veins is nominally qcr=100 ml/min when cardioplegia pressure at the HLM is 200 mmHg (27 kPa).

When retrograde cardioplegia flow rate into the coronary veins is qcr=100 ml/min coronary sinus pressure is 40 to 45 mmHg (5.2-6.5 kPa).

Aortic root suction flow rate is nominally qcs=0.5 L/min when the HLM suction pump pressure is −250 mmHg (−32.5 kPa).

In the patient simulator 2, the volume of water in the cardioplegia reservoir 86, available for aortic root suction is Vcr=300 ml. Cardioplegia solution in excess of this volume, flowing into the reservoir 86, will overflow into the venous capacitor reservoir 57, via a connection (not shown). Reverse flow from the venous capacitor reservoir 57 into the cardioplegia reservoir 86 is prevented by the configuration of the connection.

A single, typical cannula resistance to flow is simulated for each of the antegrade and retrograde cardioplegia flow paths using the resistances 82, 83, 85.

A solenoid valve 81, operated by the processing system 10 provides the mechanism for switching between the antegrade and retrograde cardioplegia resistances. The valve is operated by having the processing system 10 generate a serial control string containing a binary value, which is transferred to the controller, allowing the controller to energise the solenoid coil to open the valve.

Introduction of the cardioplegia is monitored by the pressure transducer 84 located between the two retrograde cardioplegia resistances 83, 85. Signals from the pressure transducer 84 are used by the processing system 10 to:

determine the cardioplegia flow rate and its effect on the ECG rhythms enable the software to monitor the coronary sinus pressure.

The fluid level in the cardioplegia reservoir 86 is monitored with a level switch (not shown) and this information will be used to determine if aortic root suction has been employed. The processing system 10 determines the fluid level using signals from the level switch and can use this to determine unacceptable conditions of:

antegrade cardioplegia coincident with aortic root suction; or, retrograde cardioplegia in the absence of aortic root suction.

Suction and cardioplegia flows are provided by the HLM.

Patient Thermal Mass

During surgery the HLM operates to cool and heat the blood supplied to the patient to thereby maintain patient temperature. The degree of heating and cooling required depends on the thermal mass of the patient. If it is assumed that the patient is a simple homogeneous thermal mass, there is no basal heat generated by the patient and the rate of heat loss from the patient is equal to the rate of heat gain by the blood cycling through the HLM, then the patient temperature, $T_p$ is given by:

$$T_p = \frac{1}{V_p} \int Q_b (T_v - T_a) dt$$

Where:
$V_p$=Volume of patient
$Q_b$=flow rate of blood.
$T_v$=temp. of venous blood exiting patient
$T_a$=temp. of arterial blood entering patient The volume representing the total thermal mass (Vp) is variable to simulate different sized patients up to a maximum equivalent to 20 L of water.

The thermal mass of the patient is simulated using a thermal reservoir 66 that contains water used to represent the thermal mass of a patient. The thermal reservoir 66 is coupled to the venous return line 71, thereby allowing the temperature of fluid in the venous return line 71 to be modified by mixing with water in the thermal reservoir 66. The temperature of the thermal reservoir 66 may be set before the commencement of a simulation using an appropriate heater.

In use, the processing system 10 measures the temperature of the fluid in the venous return line 71 using the temperature sensor 67. This allows the processing system 10 to a simulated patient body temperature, as well as using this for determination of mixed venous oxygen saturation.

The processing system 10 can then send a serial control string containing a binary value instruction to the controller, thereby controlling the thermal mass pump and the heater to adjust the fluid temperature as required.

In general, the initial temperature of the liquid in the venous return line 71 is 34° C. During a simulation the body temperature can be reduced to a minimum of 15° C. The minimum temperature of the flow from the heater/cooler is 10° C. and the maximum temperature is 41° C.

Flow Meter

The flow rate of blood pumped from the HLM into the patient simulator 2 is monitored using the flow meter 53. This allows the processing system 10 to determine the correct content of oxygen and other gases in the blood, and to determine the correct speed of the heart pump that will maintain the required arterial resistance.

The flow meter will measure the flow rate of water pumped from the HLM into the aortic line and typically has the following properties:

Precision: ±0.2 L/min for flow rates up to 5 L/min.
Max. flow rate: 10 L/min.
Resistance to flow: Less than 0.15 mmHg·min/L (1.2 MPa·s/m3)
Response time Step input, output shall achieve 95% of final value in 0.5 sec.

Pressure Measurement

Pressure transducers 65, 55 and 84 are used to measure CVP, arterial pressure and cardioplegia parameters respectively.

The range of the CVP transducer 65 is typically 0 to a min. of 11 mmHg (1.47 kPa) with a precision of ±0.4 mmHg (52 Pa) over this min. range.

The range of the arterial transducer 55 is typically 0 to a min. of 150 mmHg (19.5 kPa) with a precision of ±7.5 mmHg (975 Pa) over this min. range.

The range of the cardioplegia transducer 84 is typically 0 to a min. of 100 mmHg (13 kPa) with a precision of +5 mmHg (650 Pa) over this min. range.

Fault Modes

The patient simulator and other systems can be used to simulate a number of faults, and the apparatus used for this will now be described in more detail.

In each of the examples below, the fault mode is typically implemented by having the processing system 10 generate a serial control string containing an instruction, which is used by the controller to control the respective apparatus component.

Arterial Line Kink

The soft polymer tube connecting the HLM to the aorta may kink and so prevent blood flow.

This is simulated by activating the arterial line kink valve 51, which operates to block the arterial line 50. In general, the open resistance to flow is less than 0.15 mmHg·min/L (1.2 MPa·s/m3).

In any event, the perfusionist must be capable of examining the HLM 1 and detecting the change in the status of the patient simulator 2 and determine that an arterial line kink has occurred.

In practice, the perfusionist would then have to check physical lines between the HLM and the aorta to determine the fault. In this instance however the perfusionist will typically utilise the end station 5 and activate a setting indicating that an arterial line kink has been detected. This information is transferred to the processing system 10 which can then open the arterial line kink valve to thereby simulate the clearance of the blockage by the perfusionist. Alternatively, the perfusionist may be required to verbally indicate to a trainer using the processing system 10 that an arterial line kink has occurred allowing the trainer of the processing system 10 to cause the processing system 10 to open the arterial line kink valve.

It will be appreciated that in either case, the processing system 10 can record details of both the problem that has occurred and the selected solution, thereby allowing the perfusionist to subsequently review this to help identify how their technique can be improved.

Venous Line Blockage

The venous cannula may be positioned badly, preventing proper return flow to the HLM and producing a high CVP. This is simulated using the venous resistor 68 described in more detail above. Typically open resistance to flow will be less than 2 mmHg·min/L (15.6 MPa·s/m3) smoothly adjustable over its full range.

Venous Line Air Entrainment Valve

Air may enter the venous cannula due to its incorrect placement by the surgeon. An on/off solenoid valve 70 allows air to enter the venous return line 71 to the HLM. A check valve will prevent water leaking from the system. The valve materials should be compatible with a saline solution in case of leakage. When open, the solenoid valve/check valve typically provide an air flow rate of $4*10-6\pm2*10-6$ m3/s (0.24±0.12 L/min).

Oxygenator Leak

Blood may leak from a faulty connection to the oxygenator. An on/off solenoid valve 98 allows water to leak from the oxygenator input or output line and empty onto the floor. The valve and leakage line typically have an open flow resistance of 80 mmHg·min/L (613 MPa·s/m3), allowing a leakage rate of approx. 3 L/min when the simulated blood pressure at the oxygenator is 250 mmHg.

Oxygenator Air Injection

Gas may leak from a faulty oxygenator into the HLM blood circuit. An on/off pneumatic solenoid valve 93 will allow pressurised gas to leak from the oxygenator gas output line into the oxygenator "blood" output line with a gas flow rate of 0.1 L/min.

HLM Gas Flow Failure

The gas supply to the oxygenator may stop. An on/off pneumatic solenoid valve 91 will allow the pressurised gas, at the oxygenator gas input line, to be stopped.

Blood Loss

The blood loss valve 58 is located in the hydraulic system, and permits blood loss from the circulation into the pleural cavity reservoir 59. Typically this allows a flow rate of 100 mL/min.

When the blood loss valve is off, there will be no leakage into the pleural cavity reservoir 59 up to a CVP of 11 mmHg. (1.47 kPa)

The pleural cavity reservoir 59 is assumed to contain the blood loss from the patient (and observed by the perfusionist as a drop in the HLM reservoir level). The plural cavity reservoir will have a maximum capacity of 2 L. After this volume of water enters the pleural cavity, further "blood loss" will overflow onto the operating table.

Blood loss may be pumped back into the HLM by use of a hand held suction tube placed by the surgeon and simulated with the hand-held suction valve 60. When the hand-held suction valve 60 is off it represents the surgeon not having placed the suction tube into the blood, in which case air is sucked into the HLM 1. Flow can only occur when the HLM pump is operated (by the trainee). Open resistance to flow will be less than 200 mmHg·min/L (1.6 GPa·s/m$^3$), i.e. 1.0 L/min at −200 mmHg.

When the handheld suction pump on the HLM is operated but the instructor has not simulated the surgeon's placement of the suction tube in the blood, air is sucked into the HLM.

This is achieved using a check valve to allow air to pass into the Hand Held Suction line and prevent water from leaking in the opposite direction. Air will enter the Hand Held Suction line when pressure drops to a value between −230 and −270 mmHg (−31 and −36 kPa) gauge.

Ancillary Equipment

Ancillary equipment 7 is used to simulate a number of additional failure modes including:
  Oxygen Supply Failure Module.
  Heart:Lung Machine Power Failure Module.
  Patient Monitor Power Failure Module.
  Heater:Cooler Power Failure Module.

Oxygen Failure Module

The oxygen failure module is used to stop gas flow to the HLM. This creates an alarm on the HLM to indicate to the perfusionist the loss of oxygen. This is achieved by having the processing system transmit a string to the controller, which in turn activates a pneumatic valve in the oxygen fail module, thereby causing a corresponding loss in oxygen pressure.

Power Failure Modules

Various power failure modules will be provided for the system to represent either a fault in the device or complete mains failure. These modules are powered from the mains present at the inlet of the power failure module and include a relay for breaking the connection to the corresponding equipment.

The processing system 10 transmits a string to the controller, which in turn activates the relay, thereby cutting off power to the equipment. This obviates the need to modify the HLM or the like, although other arrangements could be used.

In use, when the processing system 10 simulates such a fault, the processing system 10 will activate the relay by transferring a control string to the controller 11.

In this instance, the perfusionist must take appropriate action allowing the processing system 10 to restore power to the HLM, or to complete the procedure without power to the specific device.

Setup

The patient simulator can be used in the operating room of any modern cardiothoracic surgical unit and can be connected to existing perfusion and monitoring equipment. This allows the patient simulator to re-create a wide variety of critical events which may occasionally complicate the process of cardiopulmonary bypass.

In use, the cardiovascular system components of the patient simulator will be hidden from the view of the trainee by means of drapes, which are provided by the instructor/simulation centre. Therefore, no visual clues of cardio vascular functions (such as blood loss to the thoracic cavity) are provided by the cardio vascular module.

The operation of all components within the simulator should be sufficiently quiet that the trainee is not alerted to changes that should be monitored on instruments.

The patient simulator is initially configured by providing water in the hydraulic system by filing the venous capacitor reservoir to a predetermined level, before bleeding any air from the system.

Processing System Operation

The operation of the processing system 10, and in particular the interaction with a trainer or other operator will now be described in more detail.

In particular, the processing system 10 operates to generate a graphical user interface (GUI) having the main functions that can be provided by the apparatus grouped using tab pages, and a menu system for access to the main system options, configuration and help.

This allows the trainer to select various control parameters, which in turn cause the processing system 10 to determine an appropriate response using a predetermined model. The processing system 10 uses the model to determine how the patient simulator 2 should react, and then operates to generate appropriate serial control strings which are transferred to the controller 11 to allow the corresponding components of the apparatus to be controlled. The serial control string generated may depend on the current settings of the patient simulator, and therefore may be determined in accordance with the current signals from the sensors.

The models used will now be described.

Physiological Model

The physiological model used to determine cardiac output and blood gas content and is based on the Frank-Starling relationship, which describes the blood pumped by the heart-lung compartment, cardiac output, in terms of the filling pressure, right atrial pressure.

In this instance, the trainer can adjusts values of patient parameters and then selects a set option, causing the processing system to generate the control strings for transfer to the controller.

Patient Thermal Model

The patient thermal model allows calculation of the patient thermal behavior during the perfusion, without the need to actually cool and heat the patient. This model will be used in Temperature Emulation mode, when simulation is performed without the Heather Cooler.

Trainer adjusts the value of initial patient temperature. During the simulation Trainer adjusts the pump temperature, and SPS application calculates the Arterial, Cardiac, Patient, and Venous temperatures.

Pharmacokinetic Model

The application will provide the models for patient response to drugs commonly used during the perfusion.

The Trainee will select drug type, dosage, and the infusion rate if applicable. The SPS application will calculate the Patient response to the selected drug, and adjust the patient parameter displays accordingly.

Examples of the GUIs are shown in FIGS. 10A to 10E, as will be described in more detail below. These are provided for the purpose of example only are not intended to represent the exact GUI layout or look and feel of the final product.

Figure 10A:
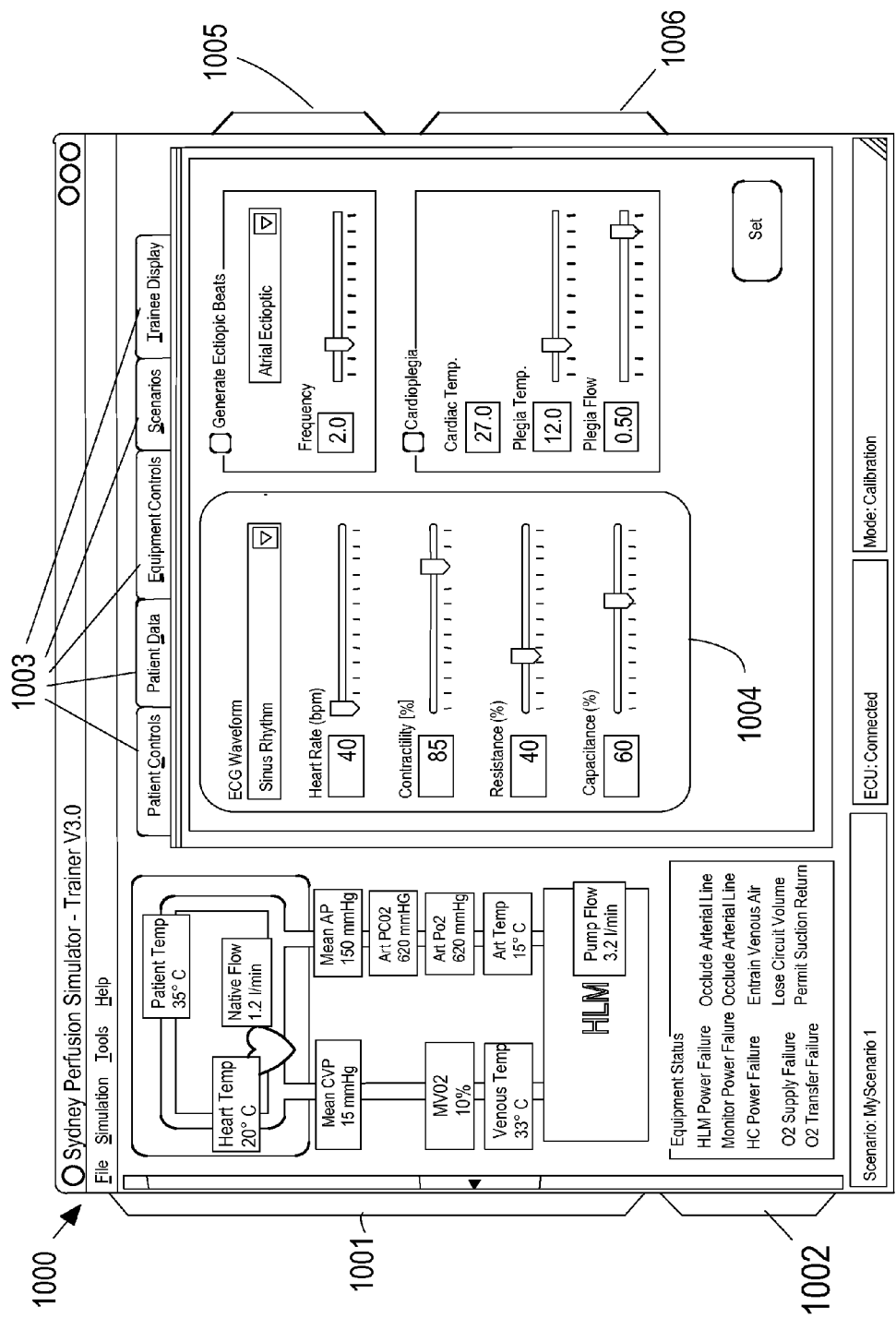
FIGS. 10A to 10E are examples of the graphical user interface of the processing system of FIG. 1; and, FIG. 11 is an example of the graphical user interface of the end station of FIG. 1; and, FIG. 12 is a schematic of an example of an alternative cardiopulmonary circuit for the patient simulator of FIG. 1.

As shown in FIG. 10A, the GUI 1000, includes a display portion 1001 which shows indicators of patient health status parameters based on readings from the sensors in the patient simulator 2. An equipment status display is provided at 1002, which is used to indicate any faults current selected.

The GUI 1000 also includes a number of tabs pages 1003, which allow the trainer to view a number of different control interfaces, as will be described in more detail below.

Patient Controls Tab Page

An example of the patient controls tab page is shown in FIG. 10A. This includes a number of patient controls 1004, a generate ectiopic beats display 1005 and a cardioplegia display 1006. This allows the trainer to make adjustments to the settings, with the processing system generate appropriate control strings based on commands stored in an LUT.

GUI provides an interface with the patient simulator 2 to perform the following functions:
  Switch On/Off the Patient Simulator power
  Set the heart rate (40-130 bpm)
  Select the type of heart rhythm (Sinus Rhythms Ventricular Fibrillation, Asystole, Atrial Ectopic, Ventricular Ectopic, P-waves only, ST Elevation, ST Depression, Diathermy)
  Enable/disable the ectopic heart beats and select the type (Atrial, Ventricular) and frequency (1-10 Hz)
  Set the heart contractility (0-100%)
  Set the Arterial Resistance (0-100%)
  Set the Venous Capacitance (0-100%)

Patient Data Tab Page

Figure 10B:
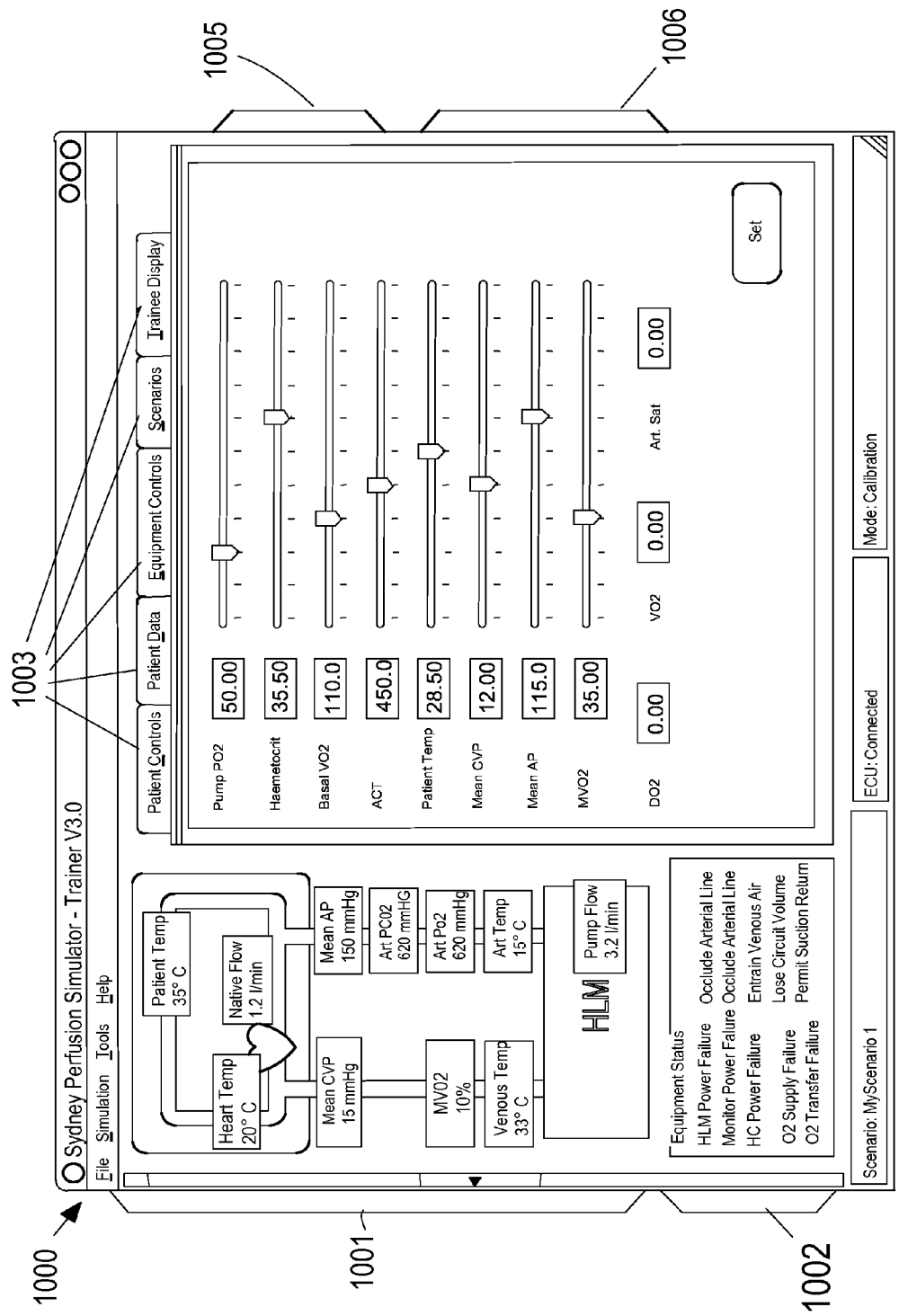
Figure 10C:
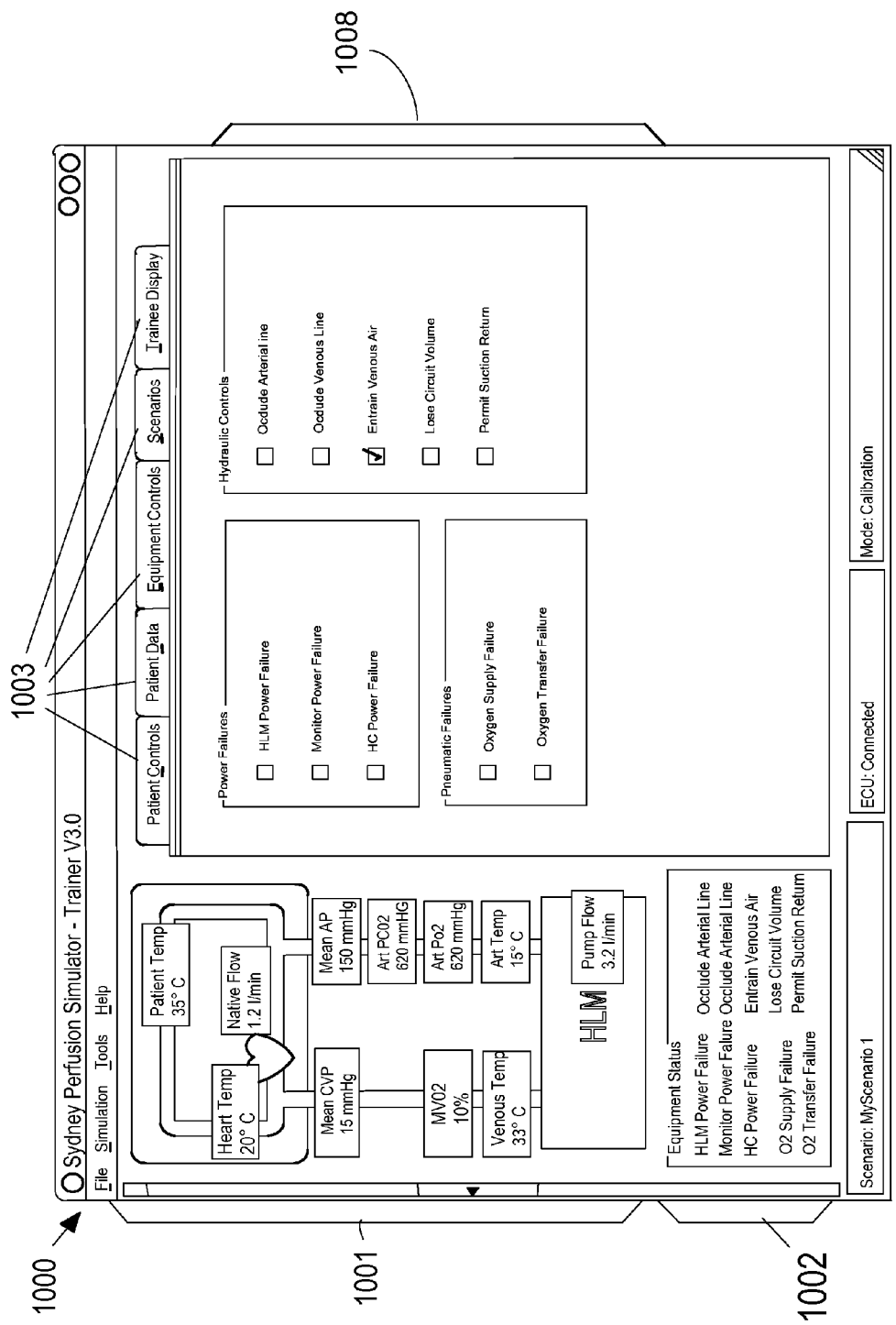

An example of the patient data tab page is shown in FIG. 10B. In this example, the GUI provides an interface to allow control of the physiological and pharmacokinetic models using the controls 1007. This allows the trainer to:

- Set the Pump PO2 (Pump Oxygen Partial Pressure 0-760 mmHg)
- Set the Haematocrit (0.0-50.0%)
- Set the Basal Oxygen Utilisation (0-999 mls/min at 37° C.)
- Set the Active Clotting Time (0-999 sec)
- Display/Set the Mean Central Venous Pressure, depending on the mode of operation (0-20 mmHg)
- Display/Set the Mean Arterial Pressure, depending on mode of operation (0-200 mmHg)
- Display/Set the Mixed Venous Oxygen Saturation, depending on mode of operation (0-100%)
- Display Total Flow Q, Native+Pump (l/min)
- Display Native Cardiac Flow (l/min)
- Display Pump Flow (l/min)
- Display Delivery of oxygen, DO2 (mls/min)
- Display Oxygen Utilisation VO2 (mls/min)
- Display Venous Saturation (0-100%)
- Display Arterial Saturation (0-100%)

Equipment Controls Tab Page

Figure 10D:
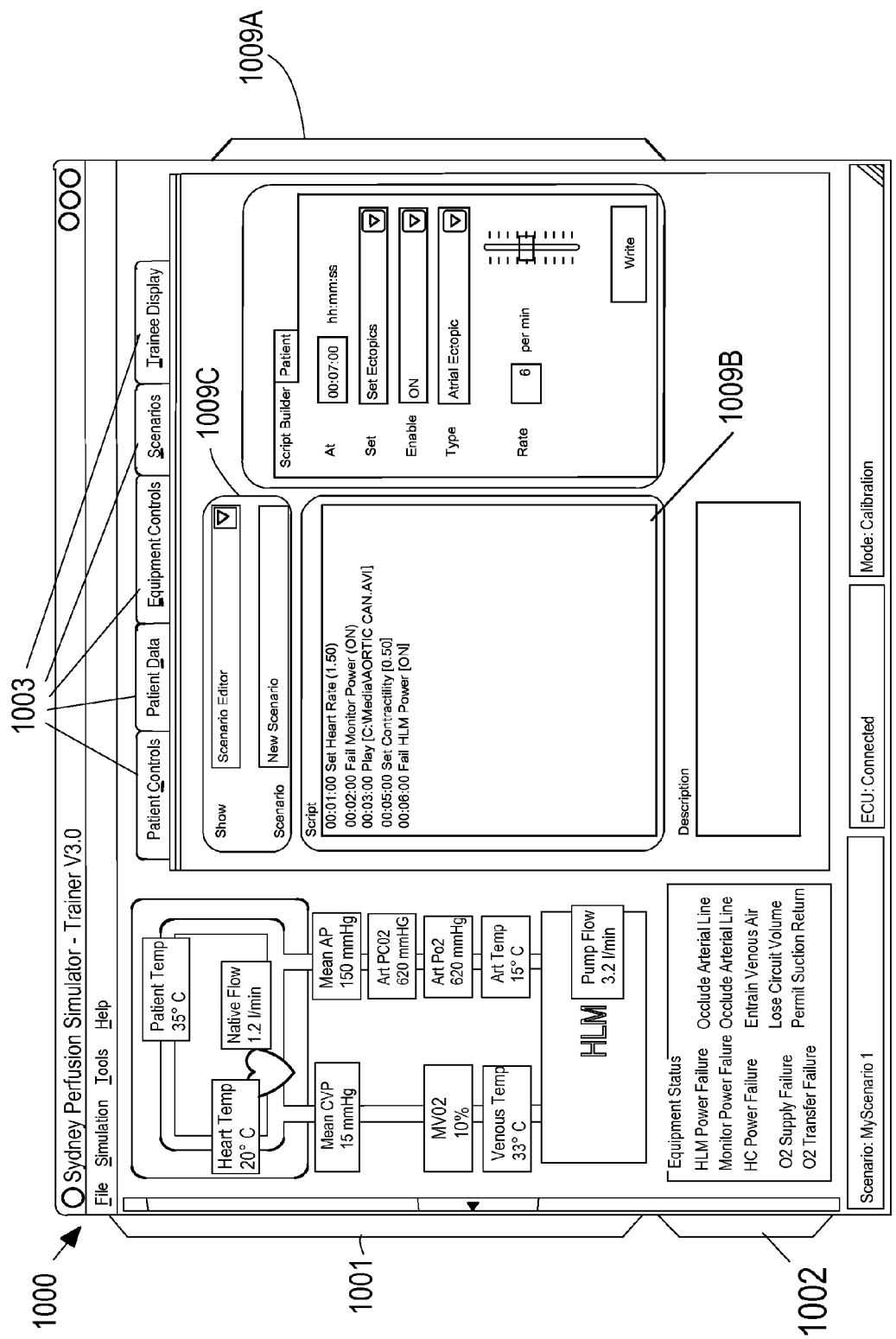

The equipment controls tab page allows the trainer to control the simulated equipment faults via the controls 1008, including:

- Heart Lungs Machine Power Failure
- Monitor Power Failure
- Heater/cooler Power Failure
- Oxygen Power Failure
- Oxygen Transfer Failure
- Arterial Line Kink
- Venous Line Kink
- Entrain Venous Air
- Lose Circuit Volume
- Permit Suction Return Scenarios Page The play/edit scenarios tab page shown in FIG. 10D includes a number of controls 1009A that provide the following functionality:

- Create/Edit Scenario
- Load/Save Scenario
- Play/Pause/Stop Scenario
- Show Scenario progress The scenarios are defined by having the operator select a time and an event that is to occur at the respective time, using a drop down list. Various parameters regarding the event can then be set using appropriate fields. Once the event has been defined, this is added to the event sequence script shown generally at 1009B.

When scenarios are being executed, the operator can select an available scenario, or choose to define a new scenario using the controls 1009C.

Control Trainee Interface

Figure 10E:
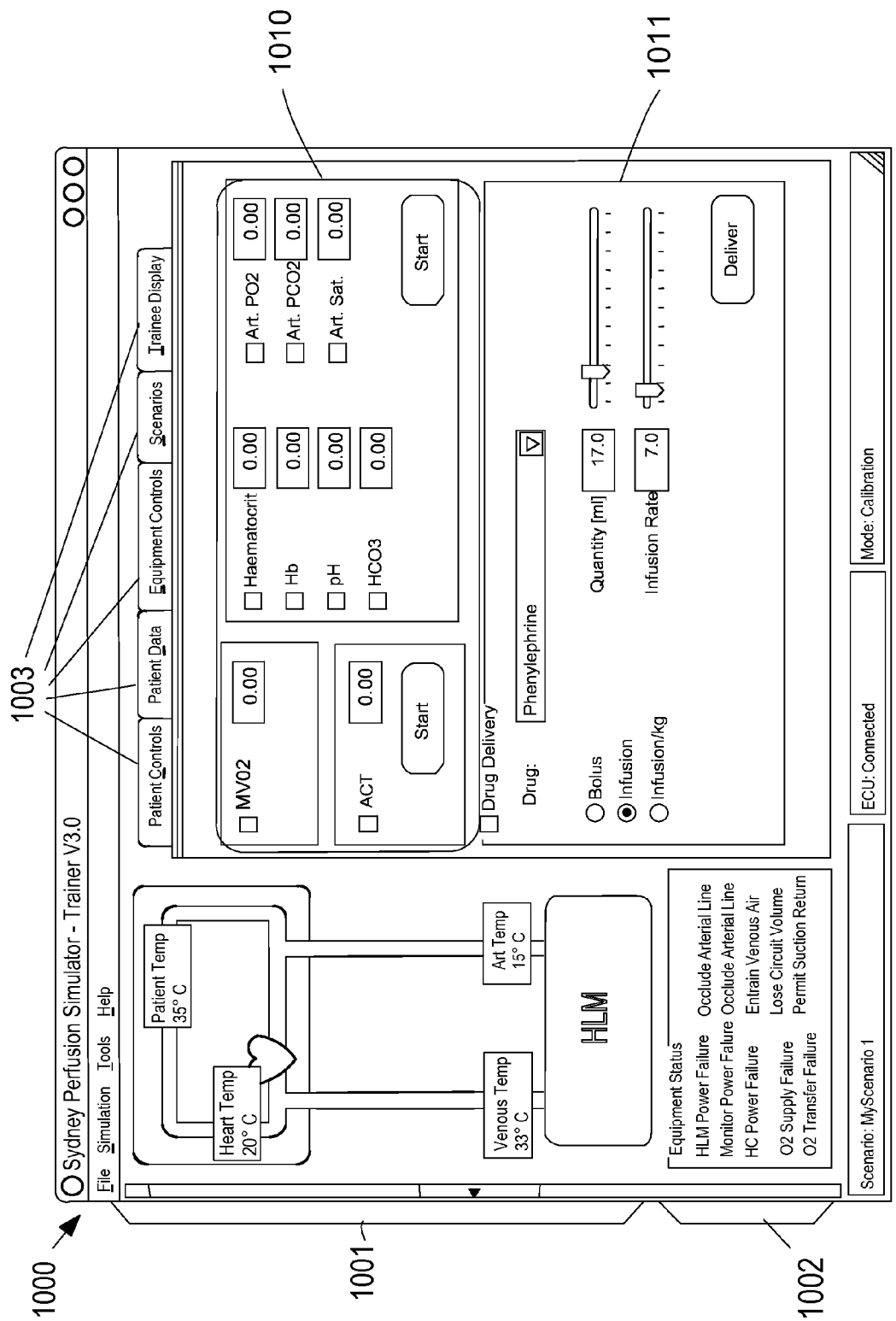

The trainee display tab page shown in FIG. 10E allows the trainer using the processing system 10 to observe and control the trainee user interface.

The page includes controls which allow the information displayed to the trainee to be manipulated, including:

- Observe/Enable/Disable Trainee Blood Analysis displays 1010;
- Observe/Enable/Disable Trainee Drug Delivery controls 1011; and,
- Print Blood Analysis results.

Trainee Interface

Figure 11:
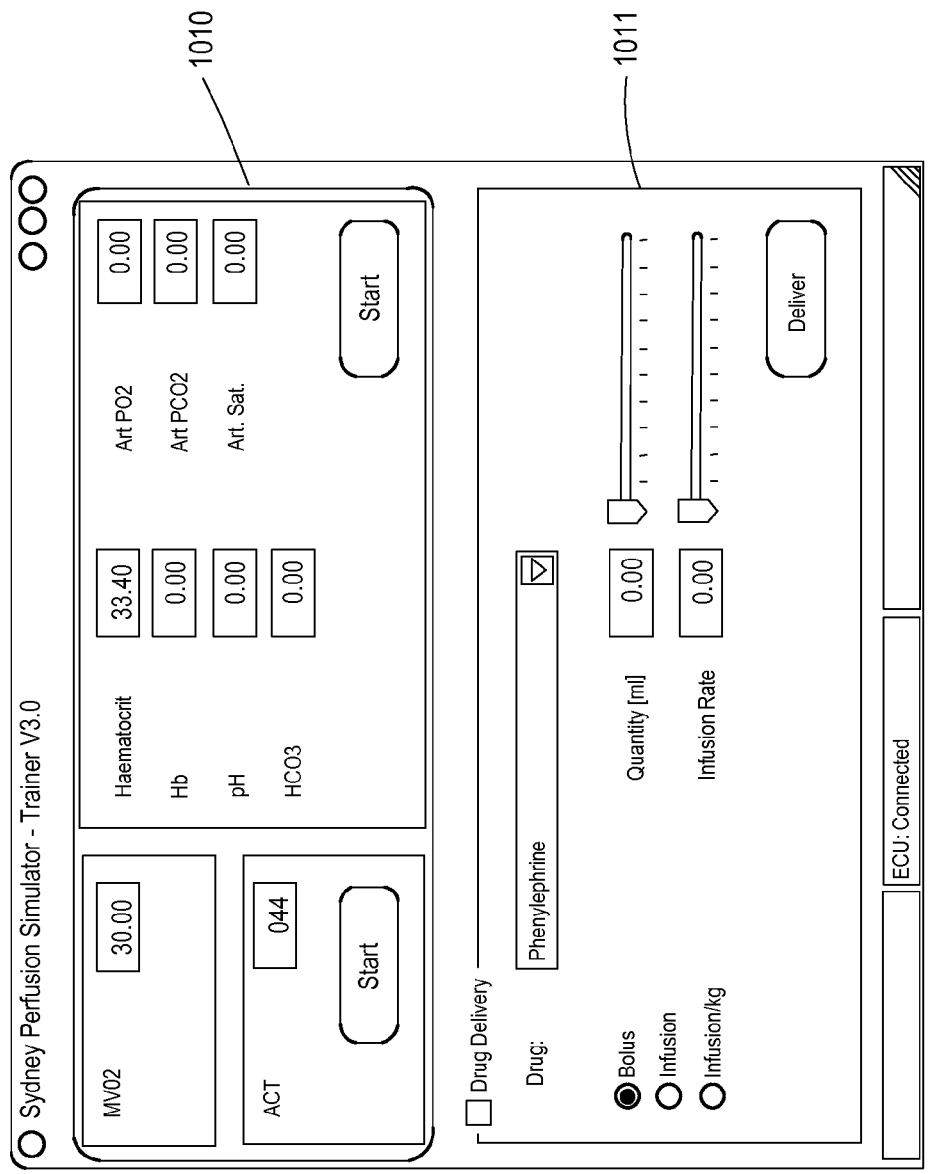

The trainee GUI is displayed to the trainee via the end station 5 is shown in FIG. 11 and provides the following displays and controls:

- Display blood analysis results 1012; and,
- Drug Delivery controls 1013.

Operating Modes

The SPS application will operate in the following modes of operation:

- Full Simulation Mode
- Temperature Emulation Mode
- Service Mode
- Manual Control Mode.

Full Simulation Mode

In this mode of operation the SPS application provides full control and monitoring of the Patient Simulator and enables the following functions:

- The physiological model of the patient oxygenation and cardiac function.
- The pharmacokinetic model.
- Trainer
  - The generation of equipment failures
  - The configuration and execution of simulation scenarios.
  - The ability to store and/or replay simulation events
- Trainee
  - Audio-visual prompting
  - Simulating drug delivery The following parameters are received from the Patient Simulator sensors:

- Patient Temperature
- Arterial Temperature
- Venous Temperature
- Mean CVP
- Mean AP
- Cardioplegia pressure
- Cardioplegia level sensor
- Pump Flow The following parameters are entered by trainer into the processing system 10 using the GUI:

- Pump PO2
- Haematocrit
- Basal VO2
- ACT

The following parameters are calculated by the processing system 10:

- Total Flow Q
- DO2
- VO2
- Venous Saturation
- Arterial Saturation

The following Equipment Control modes are communicated to controller and applied to the equipment:

- HLM Power Failure
- HC Power Failure
- Monitor Power Failure
- Occlude Arterial Line
- Occlude Venous Line
- Entrain Venous Air
- Lose Circuit Volume
- Permit Suction Return The following Control Mode is applied to both the equipment via the controller 11, and to the physiological model implemented by the processing system 10:

- Oxygen Supply Fail: Closing of the oxygen supply valve may trigger an alarm on the HLM. The physiological model will calculate the effect on blood gas content.

The following Control Mode is applied in the SPS application physiological model only:
  Oxygen Transfer Fail: The physiological model will calculate the effect on blood gas content. The effect will be identical to that for Oxygen Supply Fail.

Temperature Emulation Mode

This mode of operation is the same as Full Simulation mode, except for the following differences:
  This mode allows operation without the Heater/Cooler unit, and without the need to heat the Patient Simulator before the simulation. The displayed Patient, Venous, and Arterial temperatures are calculated by the SPS application and displayed on the trainee display.
  Trainer manually sets the values of patient simulator temperature sensor readings.
  Temperature related failure modes are simulated instead of activating the appropriate actuators.

In this mode of operation the processing system 10 provides the following functions:
  Provide the physiological model of the patient heart.
  Provide the Trainer with facilities to set the patient temperature
  Provide the pharmacokinetic model of the patient.
  Provide the Trainer with facilities for introducing the equipment failures and simulated equipment failures.
  Provide the Trainer with facilities to enter the data to substitute the values of Patient Simulator sensors.
  Provide the Trainer with facilities for configuration and execution of simulation scenarios.
  Provide the Trainee with audio-visual prompts in the form of audio and/or video clips.
  Provide the Trainee with facilities for simulated drug delivery.
  Provide the Trainer with facilities for storing and replaying of the simulation events including the Patient Controls and Data, Equipment Controls and audio visual recording.
  Equipment controls behave the same as in Full Simulation Mode. The fault modes are the same as in Full Simulation mode with the following exception:
    HC Power Failure is simulated by the processing system (since HC is not operated)

Service Mode

This mode of operation will be used for calibration and diagnostic analysis of the Patient Simulator, software testing and support.

Hydraulic System

It will be appreciated that the particular configuration of hydraulic system described in the above example of the patient simulator 2 is for the purpose of example only, and a range of variations are possible.

Thus, in the above examples, the hydraulic system shown in FIG. 4 includes a number of elements which interact to represent the compliance and resistance of a patient undergoing heart surgery, and any suitable combination of control devices and fluid flow paths could be used for this purpose.

For example, the use of a recirculating flow path, in which fluid is returned to the HLM after passing through the patient simulator 2 could be replaced with a non circulatory system, in which fluid supplied to the HLM inlet 41, and received from the HLM outlet 40 independently. In this instances fluid supplied to the HLM inlet 41 would be received from a source, such as a tap, and be controlled, using suitable control devices, to achieve a flow similar to that obtained from a patient. Similarly fluid supplied via the HLM outlet 40, would be allowed to drain after passing through control elements which introduce appropriate resistances, or the like.

Figure 12:
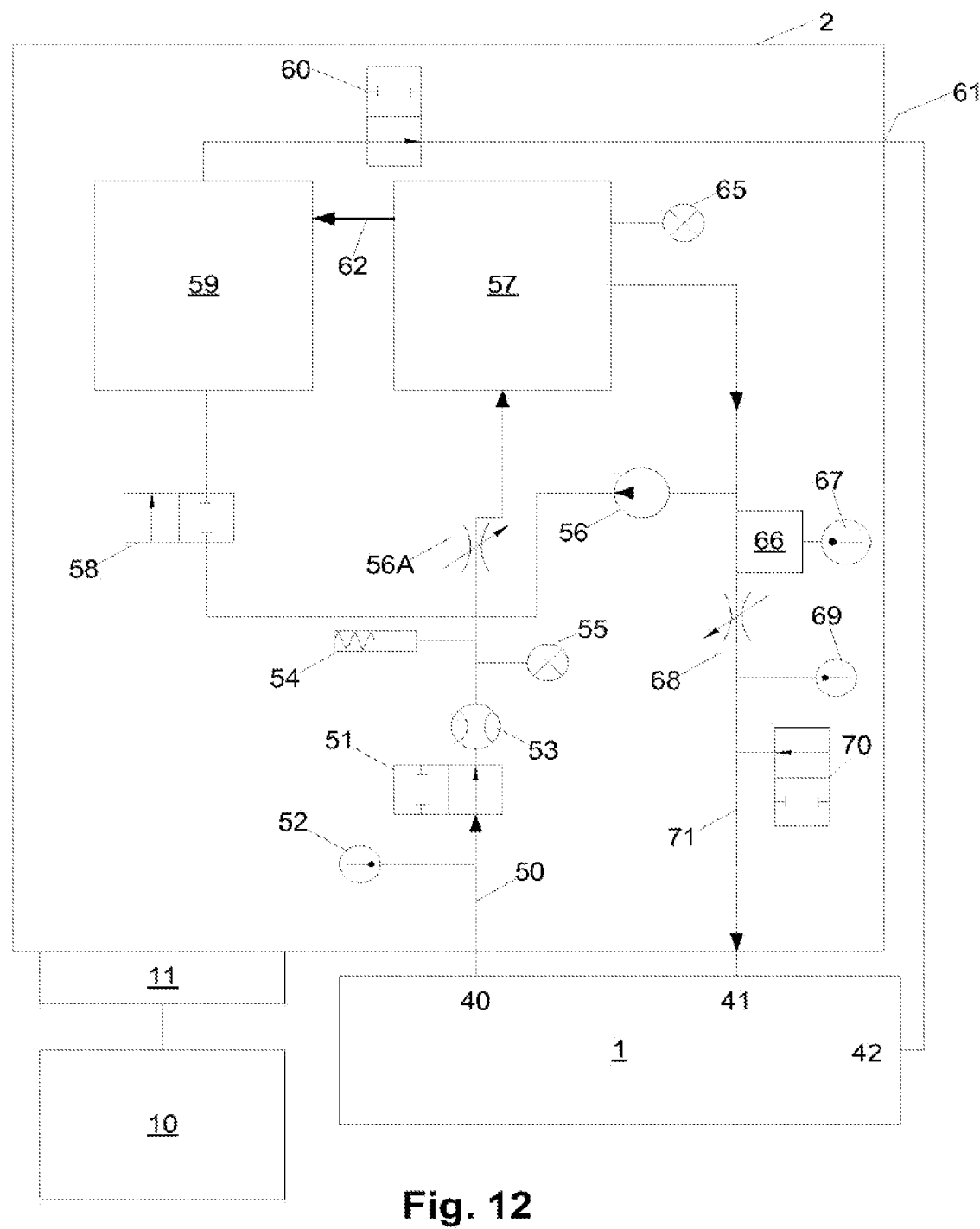

An example of an alternative arrangement is shown in FIG. 12. In this example, the heart pump 56 is placed between an outlet of the venous capacitor fluid reservoir 57, and pumps fluid back into the arterial inlet line 50. This can be used to generate the required pressure waveform, which is detected by the pressure transducer 55, as shown. In this instance an additional arterial resistor 56A is provided to simulate the patient's arterial line resistance.

Use

The system described above can be used to:
  generate a realistic circulatory system that can be perfused using a HLM and monitored using existing patient monitoring equipment.
  create a system that generates equipment failures that will simulate common scenarios related to crisis management.

The system typically includes three main components including:
  a computer containing a software package used to form the physiological model of the patient and act as the control interface for the teacher,
  an electronic control system and
  a pneumatic/hydraulic system to simulate the behaviour of a patient.

The system typically incorporates the appropriate hydraulic, electrical, physiological, pharmacokinetic and pharmacodynamic models and function as a complete 'patient substitute'.

The system can be used in the operating room of any modern cardiothoracic surgical unit and can be connected to most of the currently available perfusion and monitoring equipment. The simulation system can convincingly re-create a wide variety of critical events which may occasionally complicate the process of cardiopulmonary bypass.

The system can therefore be used in a number of different scenarios, such as providing training or other assessment of a perfusionist and other medical or paramedical staff in the use of 'heart-lung' machines and related equipment.

This allows perfusionists to train and consequently better manage mistakes or faults that arise. In addition to this, the system can be used in:
  Training in Perfusion Crisis Resource Management (PCRM)
  'Ab initio' training of perfusionists.
  Proficiency checking of experienced perfusionists.
  Continuing education of experienced perfusionists.
  Recertification.
  Demonstration of bypass techniques to surgeons and anaesthetists.
  Evaluation of new circuits or equipment.

The system can also provide the trainee with audio-visual prompts in the form of audio and/or video clips to enhance the realism of the simulation. The system will be supplied with basic clip 'libraries' which reproduce most of the activities which occur during the conduct of adult cardiac surgery. These libraries can be modified by the inclusion of institutional audio-visual clips if needed.

The system can record data from the simulator and permits subsequent analysis of the entire simulation.

However, it will be appreciated that the system can also be used in testing HLM and other related equipment, which is particularly useful for testing new designs of equipment, or testing equipment following repair or the like. Additionally, the system may be used to provide demonstrations of HLM and perfusion procedures, or the like.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A method for use with a perfusion system that has an inlet for receiving deoxygenated fluid, oxygenates the fluid and pumps oxygenated fluid out an outlet, the method comprising:

providing an apparatus that includes an inlet line that is configured to receive fluid from the outlet of the perfusion system, an outlet line that is configured to transfer fluid received via the inlet line to the inlet of the perfusion system, at least one sensor for measuring at least one fluid property of the fluid as it is transferred from the inlet line to the outlet line, at least one control device coupled to at least one of the inlet line and the outlet line, at least one fault device, and a control system operably coupled to the at least one control device, the at least one sensor and the at least one fault device;

coupling the inlet line of the apparatus to the outlet of the perfusion system, and coupling the outlet line of the apparatus to the inlet of the perfusion system;

operating the apparatus in conjunction with a perfusion process involving the perfusion system, wherein the control system controls the at least one control device based at least partially on signals from the at least one sensor so that the at least one control device manipulates the at least one fluid property as the fluid is transferred from the inlet line to the outlet line, in order to simulate characteristics of the circulatory system of the human that are responsive to fluid flow therethrough as supplied by the perfusion system during the perfusion process, and wherein the control system controls the fault device to simulate a fault in the perfusion system.

* * * * *